US008969298B2

(12) United States Patent
Matsumoto et al.

(10) Patent No.: US 8,969,298 B2
(45) Date of Patent: Mar. 3, 2015

(54) LIQUID PREPARATION OF PHYSIOLOGICALLY ACTIVE PEPTIDE

(75) Inventors: Masaru Matsumoto, Gunma (JP);
Masako Matsumoto, Gunma (JP);
Takeshi Hanada, Saitama (JP); Naomi Wakabayashi, Gunma (JP)

(73) Assignees: Daiichi Sankyo Co., Ltd., Tokyo (JP);
Kenji Kangawa, Osaka (JP)

( * ) Notice: Subject to any disclaimer, the term of this patent is extended or adjusted under 35 U.S.C. 154(b) by 19 days.

(21) Appl. No.: 12/848,638

(22) Filed: Aug. 2, 2010

(65) Prior Publication Data

US 2011/0077195 A1 Mar. 31, 2011

Related U.S. Application Data

(62) Division of application No. 11/660,406, filed as application No. PCT/JP2005/015362 on Aug. 24, 2005, now abandoned.

(30) Foreign Application Priority Data

Aug. 24, 2004 (JP) ................................. 2004-244339

(51) Int. Cl.
*A61K 38/02* (2006.01)
*A61K 9/00* (2006.01)
*A61K 38/25* (2006.01)
*A61K 47/10* (2006.01)
*A61K 47/12* (2006.01)
*A61K 47/22* (2006.01)
*A61K 47/26* (2006.01)
*A61K 47/40* (2006.01)

(52) U.S. Cl.
CPC ............... *A61K 9/0019* (2013.01); *A61K 38/25* (2013.01); *A61K 47/10* (2013.01); *A61K 47/12* (2013.01); *A61K 47/22* (2013.01); *A61K 47/26* (2013.01); *A61K 47/40* (2013.01)
USPC .......................... 514/11.3; 514/11.4; 530/300

(58) Field of Classification Search
None
See application file for complete search history.

(56) References Cited

U.S. PATENT DOCUMENTS

| 5,503,827 A | 4/1996 | Woog et al. |
| 6,967,237 B2 | 11/2005 | Bednarek |
| 2002/0061838 A1 | 5/2002 | Holmquist et al. |

FOREIGN PATENT DOCUMENTS

| CA | 2 471 879 | 11/2003 |
| EP | 199992 | 11/1986 |
| EP | 1 506 786 | 2/2005 |
| JP | 61-221125 | 11/1986 |
| JP | 02-096533 | 4/1990 |
| JP | 07-252162 | 10/1995 |
| JP | 08-505617 | 6/1996 |
| JP | 08-283176 | 10/1996 |
| JP | 00/15224 | 3/2000 |
| JP | 2001-500876 | 1/2001 |
| JP | 2002-524514 | 8/2002 |
| JP | 03/002136 | 1/2003 |
| JP | 03/097083 | 11/2003 |
| JP | 2004-513069 | 4/2004 |
| WO | WO 95/01185 | 1/1995 |
| WO | WO 01/92292 A2 | 12/2001 |

OTHER PUBLICATIONS

Gong et al., Canadian Water Resources Journal.*
Egleton and Davis, Peptides, 1997; 18: 1431-1439.*
Gong et al., Canadian Water Resources Journal. 2000; 25: 407-422.*
Nishikimi et al., Effects of Long-Term Intravenous Administration of Adrenomedullin (AM) Plus hANP Therapy in Acute Decompensated Heart Failure, Circ. J., 73:892-898 (2009).
Tschöp et al., Ghrelin Induces Adiposity in Rodents, Nature, 407:908-913 (2000).
Aryat et al., "Endocrine activities of ghrelin, a natural growth hormone secretagogue (GHS), in humans: comparison and interactions with hexarelin, a nonnatural peptidyl GHS, and GH-releasing hormone," Journal of Clinical Endocrinology and Metabolism, Mar. 2001, vol. 86(3), p. 1169-74.
Eckert Animal Physilogy: Mechanisms and Adaptations (1997) pp. 532-535, Figure 13-18.
Elipe et al., H NMR Structural Analysis of Human Ghrelin and Its Six Truncated Analogs, Biopolymers, vol. 59, pp. 489-501 (2001).
Hosoda et al; *Purification and Characterization of Rat des-Gln$^{14}$-Ghrelin, a Second Endogenous Ligand for the Growth Hormone Secretagogue Receptor,* The Journal of Biological Chemistry; vol. 275, No. 29, Issue of Jul. 21, pp. 21995-2200, (2000).
Hosada et al., (2004) Clinical Chemistry 50(6): 1077-1080.
Isimaru et al., "Stability of the octanoyl group essential for expressing the biological activities of rat ghrelin," Peptide Science 2002, Mar. 2003, 157-160.
Kanamoto et al., (2001) The Journal of Clincal Endocrinology & Metabolism 88(10): 4984-4990.
Matsumoto et al. Biochemical and Biophysical Research Communications, 2001, vol. 287, 142-146.

(Continued)

*Primary Examiner* — Christina Borgeest
(74) *Attorney, Agent, or Firm* — Hunton & Williams LLP

(57) ABSTRACT

An effective liquid preparation achieves high bioavailability (BA) of physiologically active peptides or proteins, including ghrelins, that are administered as drugs. Also provided is a method for improving the BA of physiologically active peptides or proteins, including ghrelins, that are subcutaneously injected in aqueous solutions. The liquid preparation contains: a physiologically active peptide or protein, such as ghrelins, as an active ingredient; an acid solution including one or a combination of two or more selected form the group consisting of acetic acid, lactic acid, phosphoric acid, glycine, citric acid, hydrochloric acid, propionic acid, butyric acid, benzoic acid and salts thereof; an alcohol; and a polar organic liquid including one or a combination of two or more selected from the group consisting of N-methyl-2-pyrrolidone, dimethylformamide, dimethylsulfoxide and methylparaben.

10 Claims, 4 Drawing Sheets

(56) References Cited

OTHER PUBLICATIONS

Peino et al., "Ghrelin-induced growth hormone secretion in humans," European Journal of Endocrinology, Nov. 2000, vol. 143(5), r11-14.
Seoane et al., "Ghrelin elicits a marked stimulatory effect on GH secretion in freely-moving rats," European Journal of Endocrinology, Nov. 2000, vol. 143(5), R7-9.
Voet & Voet Biochemistry, 1995, ($2^{nd}$ Ed.) John Wiley & Sons, Inc. p. 60-62 and 77.
"www.answers.com—saline" (Oct. 14, 2009).
"wikianswers.com—pH of physiological saline?" (Oct. 14, 2009).
"www.britannica.com—saline" (Oct. 14, 2009).
The Alliance for Cellular Signaling (AfCS) Ringer's Solution Protocol (Oct. 14, 2009) www.signaling-gateway.org.

* cited by examiner

LIQUID PREPARATION OF PHYSIOLOGICALLY ACTIVE PEPTIDE

This application is a divisional application of U.S. patent application Ser. No. 11/660,406, filed Feb. 16, 2007 now abandoned; which is a National Stage Filing of International Patent Application No. PCT/JP2005/015362, filed Aug. 24, 2005, which claims the benefit of priority to Japanese Patent Application No. JP 2004-244339, filed Aug. 24, 2004, the disclosures of each of which are herein incorporated by reference in their entireties.

TECHNICAL FIELD

The present invention relates to a liquid preparation of a physiologically active peptide or a physiologically active protein with improved bioavailability, as well as to a method for improving the bioavailability of a physiologically active peptide or a physiologically active protein.

BACKGROUND OF THE INVENTION

Pharmaceutical preparations of a variety of physiologically active peptides or physiologically proteins are currently available in the market place. Among such physiologically active peptides or physiologically proteins are insulin, growth hormones, atrial natriuretic peptide, calcitonin, LHRH analogues, parathyroid hormone, and adrenocorticotropic hormone derivatives. Since these compounds are deactivated in the gastrointestinal tract by the action of proteases, they are rarely administered in oral preparations; most are formulated as parenteral preparations such as injections for clinical use.

Continuous, long-term treatment of diseases by injection requires patients to visit a hospital or clinic to receive treatment and poses a significant burden to patients. Thus, subcutaneous injections that patients can administer themselves have been desired. Drugs administered by subcutaneous injection, however, are decomposed by proteases during the subcutaneous absorption process and their bioavailability generally becomes lower than is achieved by intravenous injection.

To compensate for the low bioavailability of drugs, currently used subcutaneous injections contain increased doses of drugs or require frequent administration as compared to the intravenous administration. Thus, subcutaneous injections still remain stressful to patients. As used herein, the term "biological availability (EA)" refers to how much of the administered drug reaches the blood circulation (also referred to as extent of bioavailability (EBA)).

Ghrelin, an endogenous growth hormone secretagogue (GHS) that binds to growth hormone secretagogue receptor (GHS-R), is a physiologically active peptide first isolated from rat stomach in 1999 (Non-Patent Document 1). Ghrelins with similar primary structures were later isolated from, or suggested by cDNA analysis to be present in, other vertebrates, including human, mice, pigs, chickens, eel, cows, horses, sheep, frogs, rainbow trout and dogs. Their primary structures were shown in Table 1. Ghrelin has also been isolated from cats and goats.

TABLE 1

| Human | GSS(n-octanoyl)FLSPEHQRVQQRKESKKPPAEIQPR |
| | GSS(n-octanayl)FLSPEHQRWREESKKPPAKLQPR |
| Rat | GSS(n-octanoyl)FLSPEHQKAQQRKESEKPPAKLQPR |
| | GSS(n-octanoyl)FLSPEHQKAQREESKKPPAKLQPR |
| Mouse | GSS(n-octanoyl)FLSPEHQKAQQREESKKPPAKLQPR |
| Porcine | GSS(n-octanoyl)FLSPEHQKVQQRKESEXPAAKLKPR |
| Bovine | GSS(n-octanoyl)FLSPEHQKLQRKEAKKPSGRLKPR |
| Ovine | GSS(n-octanoyl)FLSPEHQKLQREEPKKPSGRLKPR |
| Canine | GSS(n-octanoyl)FLSPEHQKLQQREESKKPPAKLQPR |
| Eel | GSS(n-octanoyl)FLSPSQRPQGRDEYPPRV-NH$_2$ |
| Trout | GSS(n-octanoyl)FLSPSQKPQVRQGKGKPPRV-NH$_2$ |
| | GSS(n-octanoyl)FLSPSQKPQGKGKPPRV-NH$_2$ |
| Chicken | GSS(n-octanoyl)FLSPTYKNIQQQEGTRKPTAR |
| | GSS(n-octanoyl)FLSPTYKNIQQQEDTRKPTAR |
| | GSS(n-octanoyl)FLSPTYKNIQQQEDTRKPTARLH |
| Bullfrog | GLT(n-octanoyl)FLSPADMQKIAERQSQNKLRHGNM |
| | GLT(n-decanoyl)FLSPADMQKIAERQSQNKLRHGNM |
| | GLT(n-octanoyl)FLSPADMQKIAERQSQNKLRHGNMN |
| Tilapia | GSS(n-octanoyl)FLSPSQKPQNKVKSSRI-NH$_2$ |
| Catfish | GSS(n-octanoyl)FLSPTQKPQNRGDRKPPRV-NH$_2$ |
| | GSS(n-octanoyl)FLSPTQKPQNRGDRKPPRVG |
| Equine | GSS(n-butanoyl)FLSPEHHKVQHREESKKPPAKLKPR |

(In Table 1, amino acid residues are indicated by IUPAC/TUC single letter codes.)

Endogenous ghrelin found in these animals is a peptide that has a unique hydrophobic modified structure in which the serine (S) or threonine (T) residue at position 3 is acylated with a fatty acid such as octanoic acid and decanoic acid. Ghrelin binds to growth hormone secretagogue receptor to increase the intracellular level of calcium ions. Studies have revealed that ghrelin is a potent growth hormone secretagogue that modulates the secretion of growth hormone. Thus, the physiological roles and potential pharmaceutical applications of ghrelin have attracted significant interest (Patent Document 1). In the present invention, all types of naturally occurring ghrelins are collectively referred as "ghrelin."

Ghrelin derivatives or analogues obtained by partial deletion or substitution of natural animal ghrelin have also drawn much attention as treatment for various diseases (Patent Document 3).

In ghrelin derivatives, the hydrophobic modified structure does not contain an octanoyl group ($C_8$) as in natural ghrelin, but a different modified structure, such as that containing a fatty acid having 2 to 20, preferably about 4 to 12 carbon atoms, including, for example, a hexanoyl group ($C_6$), a decanoyl group ($C_{10}$) and a dodecanoyl group ($C_{12}$), that containing a fatty acid branched or unsaturated derivatives thereof, that containing an aromatic ring, such as a phenylpropionyl group, and that containing an adamantane backbone. While the hydrophobic modified structure of natural animal ghrelin is bound to the peptide backbone via an ester linkage, this linkage may be provided by an ester, ether, thioether, amide, or disulfide linkage in ghrelin derivatives (Patent Document 1).

Despite high expectations for application of ghrelins comprising ghrelin, ghrelin derivatives and ghrelin analogues in pharmaceutical products, no viable pharmaceutical compositions have yet to be designed and much still remains unknown about the pharmacokinetics of the compounds.

As to the pharmaceutical compositions using ghrelins, Patent Document 2 describes the effect of pH on aqueous solutions of ghrelins, as well as a method for preventing decomposition of the hydrophobic modified structure of ghrelins. According to Patent Document 2, ghrelins are stable in an aqueous solution in a pH range of 2 to 7. The pH of the solution can be adjusted by pH adjusters and buffers. The buffer is used to minimize the pH change of the aqueous solution during storage. Among the buffers that are described in Patent Document 2 are glycine-hydrochloric acid buffer, acetic acid buffer, citric acid buffer, lactic acid buffer, phosphoric acid buffer, citric acid-phosphoric acid buffer, phosphoric acid-acetic acid-boric acid buffer and phthalic acid buffer (Patent Document 2, p. 11, lines 5-14).

In examples described in Patent Document 2, the stability of ghrelin is tested in McIlvaine buffer (a mixture of aqueous citric acid and an aqueous solution of disodium hydrogen phosphate), Britton-Robinson buffer (a mixture of aqueous phosphoric acid/acetic acid/boric acid and an aqueous sodium hydroxide solution), citric acid buffer, glycine-hydrochloric acid buffer and acetic acid buffer. While Patent Document 2 describes that the stability of ghrelins in each solution was ensured by maintaining the pH of the solution within a range of 2 to 7, nothing is mentioned about the kinetics of the compound when it is administered to patients.

In designing pharmaceutical compositions containing a peptide or a protein, it is important to ensure the stability of the peptide or the protein prior to administration since peptides and proteins are generally unstable in aqueous solutions. It is, however, more important to design a preparation that can effectively elicit the activity of the administered compound.
Patent Document 1: International Patent Publication No. WO 01/07475
Patent Document 2: International Patent Publication No. WO 03/097083
Patent Document 3: Published Japanese translation of PCT application No. 2004-514651
Patent Document 4: Japanese Patent Publication No. Sho 63-40166
Patent Document 5: Japanese Patent No. 2643426
Patent Document 6: Published Japanese translation of PCT application No. 2004-522803
Patent Document 7: Japanese Patent Publication No. Hei 2-19092
Patent Document 8: Japanese Patent Publication No. 5-24129
Patent Document 9: Japanese Patent No. 3120987
Non-Patent Document 1: Kojima at al., Nature, vol. 402, pp. 656-660, 1999
Non-Patent Document 2: Tokihiro et al., J. Pharm. Pharmacol., vol. 52, pp. 911-917, 2000

DISCLOSURE OF THE INVENTION

Problems to be Solved by the Invention

A physiologically active peptide, ghrelins are susceptible to digestion by proteases and is thus preferably administered by parenteral routes, in particular, by injection. Even when ghrelins are administered by injection, in the subcutaneous administration it is still necessary to ensure that injected ghrelin is absorbed from the injection site and reaches blood circulation. However, in general, the low BA of subcutaneously injected peptides makes it difficult to design effective injections.

Studies are currently being conducted to determine effective doses of ghrelin to obtain a particular pharmacological effect in accordance with the relationship between the administered amount of drugs and the obtained pharmacological effect as an index. It is necessary to control the blood level of drugs, as well as to establish preparation technology to increase drug absorption, for effective and safe administration of drugs.

The BA of subcutaneously injected peptides is generally known to be about 20% to 40%, which is lower than the BA of other drugs. We examined the BA of subcutaneously injected ghrelin in rats and monkeys and found that the BA of ghrelin was significantly lower than that of other subcutaneously injected peptides: at most 5% in rats and at most 3% in monkeys. No previous studies have reported this fact.

Possible factors for the change in the rate of BA of a given drug are the efficiency and the rate of transfer of the drug from the application site to nearby peripheral blood. These factors are dependent upon properties of the drug and the application site, including molecular weight, pKa and fat solubility and other physicochemical properties that determine the diffusibility of the drug in bodily fluids and tissues and the permeability of the drug through biological membranes, as well as the histological morphology and physiological properties of the application site.

A low BA of a given drug must be compensated for by increasing the dose and the frequency of administration to achieve the effective plasma level of the drug. Since this poses a significant burden to patients, preparation technology is needed to increase the BA of the drug.

Accordingly, it is an object of the present invention to ensure high BA of physiologically active peptides or proteins, including ghrelins, these are administered as drugs, and to provide an effective liquid preparation of the peptides or proteins. It is another object of the present invention to provide a method for improving the BA of physiologically active peptides or proteins, including ghrelins, these are subcutaneously injected in aqueous solutions.

Means for Solving the Problems

In an effort to achieve these objects, the present inventors examined the blood level of ghrelins after administration by injection.

Specifically, we administered ghrelin along with different auxiliary agents used in injections and monitored its BA. The auxiliary agents used included mannitol as an isotonic agent, urea as a solubilizing agent and a sodium acetate buffer (pH 4.0). These agents were mixed with ghrelin and subcutaneously injected in rats. It turned out that sodium acetate buffer (pH 4.0) significantly increased the BA to 35.3%. No significant increase in the BA was observed for the other agents tested: the greatest increase was 3.4% by urea.

We then administered ghrelin with different acidic solutions and monitored its BA. As it turned out, the BA increased for each solution tested.

We thus demonstrated that the BA of ghrelin can be significantly increased by subcutaneously injecting it with an acidic solution.

We also demonstrated that the BA of ghrelin can be controlled by varying the type, concentration and pH of the acidic solution. We also found that the BA of ghrelin can be improved to a different degree depending on the type of the acidic solution. This suggests that factors other than the type and the pH of ghrelin preparation or ghrelin solution are involved in the improvement of the BA of ghrelin.

We also found that the BA of ghrelin is significantly improved by subcutaneously injecting it with a polar organic liquid.

We also found that the increase in the BA of ghrelin is more significant when ghrelin is administered with both the acidic solution and the polar organic liquid than when it is administered with either one of the two.

We also found that the BA of ghrelin is significantly increased by subcutaneously injecting it with the acidic solution and a sugar, or with the polar organic liquid and a sugar.

We also found that the ability of the acidic solution and/or the polar organic liquid and/or the sugar to increase BA is observed not only with ghrelin, but also with other physiologically active peptides or proteins for use as drugs.

Accordingly, specific embodiments of the present invention comprises the following:

(1) A liquid preparation containing a physiologically active peptide or a physiologically active protein as an active ingredient in combination with an acidic solution;

(2) The liquid preparation according to (1) above, wherein the acidic solution comprises one or a combination of two or more selected from the group consisting of acetic acid, lactic acid, phosphoric acid, glycine, citric acid, hydrochloric acid, propionic acid, butyric acid, benzoic acid and salts thereof;

(3) The liquid preparation according to (1) above, wherein the acidic solution comprises one or a combination of two or more selected from the group consisting of acetic acid, lactic acid, propionic acid, butyric acid and/or phosphoric acid, and salts thereof;

(4) The liquid preparation according to (1) or (2) above, having a pH in the range of 3.0 to 7.0;

(5) The liquid preparation according to any of (1) to (3) above, wherein the concentration of the acidic solution is from 1 to 1000 mM;

(6) The liquid preparation according to any of (1) to (3) above, wherein the concentration of the acidic solution is from 10 to 500 mM; and (7) The liquid preparation according to any of (1) to (6) above, wherein the acidic solution is an acid buffer having a pH in the range of 3.0 to 7.0.

Other embodiments of the present invention comprises the following:

(8) A liquid preparation containing a physiologically active peptide or a physiologically active protein as an active ingredient in combination with a polar organic liquid;

(9) The liquid preparation according to any of (1) through (7) above, containing a physiologically active peptide or a physiologically active protein as an active ingredient in combination with a polar organic liquid;

(10) The liquid preparation according to (8) or (9) above, wherein the polar organic liquid is one or a combination of two or more selected from the group consisting of an alcohol and/or N-methyl-2-pyrrolidone, dimethylformamide, dimethylsulfoxide and methylparaben;

(11) The liquid preparation according to (8) or (9) above, wherein the polar organic liquid is one or a combination of two or more selected from the group consisting of benzyl alcohol, ethanol, phenol, tert-butanol, chlorobutanol, N-methyl-2-pyrrolidone, dimethylformamide and dimethylsulfoxide;

(12) The liquid preparation according to any of (8) to (11) above, wherein the concentration of the polar organic liquid is from 0.001 to 80% (w/v);

(13) The liquid preparation according to any of (8) to (11) above, wherein the concentration of the polar organic liquid is from 0.1 to 10% (w/v);

(14) The liquid preparation according to any of (1) to (7) above, further containing a sugar;

(15) The liquid preparation according to any of (8) to (12) above, further containing a sugar;

(16) The liquid preparation according to any of (1) to (7) above, further containing a polar organic liquid and a sugar;

(17) The liquid preparation according to any of (14) to (16) above, wherein the sugar is one or a combination of two or more selected from the group consisting of mannitol, sucrose, glucose and cyclodextrin;

(18) The liquid preparation according to any of (14) to (17) above, wherein the sugar is cyclodextrin; and

(19) The liquid preparation according to any of (14) to (17) above, wherein the concentration of the sugar is from 0.1 to 20% (w/v).

More specific embodiments of the present invention comprise the following:

(20) The liquid preparation according to any of (1) to (19) above, wherein the physiologically active peptide or the physiologically active protein is one selected from the group consisting of ghrelins, human glucagon-like peptide-1 (hGLP-1), human atrial natriuretic peptide (hANP), human adrenomedulin, human parathyroid hormone (hPTH(1-34)) and human insulin;

(21) The liquid preparation according to any of (1) to (19) above, wherein the physiologically active peptide or the physiologically active protein is one of ghrelins;

(22) The liquid preparation according to any of (1) to (19) above, wherein the one of ghrelins is ghrelin;

(23) The liquid preparation according to any of (1) to (19) above, wherein the ghrelin is human ghrelin;

(24) The liquid preparation according to any of (1) to (19) above, wherein the concentration of the ghrelins is from 0.03 nmol/mL to 15 μmol/mL;

(25) The liquid preparation according to any of (1) to (24) above, for use as an injection; and

(26) The liquid preparation according to (25), for use as a subcutaneous injection or intramuscular injection.

Even more specific embodiments of the present invention comprises the following:

(27) A liquid preparation, comprising: ghrelins as an active ingredient; an acid solution comprising one or a combination of two or more selected form the group consisting of acetic acid, lactic acid, propionic acid, butyric acid and/or phosphoric acid; and a polar organic liquid comprising one or a combination of two or more selected from the group consisting of benzyl alcohol, ethanol, phenol, tert-butanol, N-methyl-2-pyrrolidone, dimethylformamide and dimethylsulfoxide, wherein the liquid preparation has a pH in the range of 3.0 to 7.0; and

(28) A method for improving bioavailability of ghrelins, comprising adding an acidic solution and a polar organic liquid to an aqueous solution of ghrelins.

Effect of the Invention

According to the present invention, there is provided an effective liquid preparation that achieves high bioavailability (BA) of physiologically active peptides or proteins, including ghrelins, these are administered as drugs.

There is also provided a method for improving the BA of physiologically active peptides or proteins, including ghrelins, these are subcutaneously injected in aqueous solutions.

Thus, the present invention makes it possible to maintain the blood level of physiologically active peptides or proteins, including ghrelins, that are subcutaneously injected: To date, it has been considered difficult to maintain therapeutically effective plasma levels of subcutaneously injected peptides and proteins. The present invention therefore is of significant medical importance.

BEST MODE FOR CARRYING OUT THE INVENTION

The liquid preparation of the present invention containing as an active ingredient a physiologically active peptide or protein, such as ghrelins, will now be described in detail, as well as the method for improving the BA of a physiologically active peptide or protein.

Ghrelins for use in the present invention are endogenous growth hormone secretagogues (GHS): They are peptides that act to increase the intracellular level of calcium ions and to induce the secretion of growth hormone. The term "ghrelins" as used herein encompasses all ghrelin derivatives that result from insertion, deletion, substitution and/or addition in the amino acid sequence of the peptide backbone of ghrelin naturally occurring in animals and that have physiological activities equivalent to natural ghrelin.

Natural ghrelin for use in the present invention is preferably a natural ghrelin derived from human, rats, pigs, chickens, eel, cows, horses, sheep, frogs, rainbow trout and dogs. Ghrelin derivatives suitable for use in the present invention include those in which the serine residue at position 3 is acylated not with octanoyl group, but with a fatty acid having 4 to 12 carbon atoms, or des-octanoyl ghrelin that does not have the octanoyl modification on the serine residue at position 3.

Human ghrelin is preferably used when the liquid preparation is intended for administration to human patients.

Ghrelins may be provided in the form of a free peptide or a salt. Ghrelins in the free peptide form and the salt form can be converted into each other by common techniques. The free peptide may be converted into a pharmaceutically acceptable salt by reacting it with an inorganic acid or an organic acid. Examples of the pharmaceutically acceptable salt include salts formed with inorganic acids, such as carbonates, bicarbonates, hydrochlorides, sulphates, nitrates and borates, and salts formed with organic acids, such as succinates, acetates, propionates and trifluoroacetates.

The peptide may also form salts with inorganic bases including alkaline metals such as sodium and potassium and alkaline earth metals such as calcium and magnesium, or organic bases including organic amines such as triethylamine, and basic amino acids such as arginine. The peptide may also form a metal complex (such as copper complex and zinc complex).

Ghrelins for use in the present invention may be of any origin: It may be isolated from natural raw materials, or it may be obtained by common techniques such as chemical synthesis, chemical semisynthesis, gene recombination or combinations of these techniques. Alternatively, it may be extracted from living organisms. One example of such techniques is described in Patent Document 1.

Ghrelins may be used in the liquid preparation of the present invention at any concentration suitable for use in pharmaceutical products. Specifically, the lowest concentration of ghrelins is defined as the concentration at which it can provide the desired effect as pharmaceutical products whereas the highest concentration is defined as the concentration at which it can completely dissolve in an aqueous solution. The concentration of ghrelins in the liquid preparation is preferably in the commonly used range of about 0.03 nmol/mL to about 15 μmol/mL, and more preferably in the range of about 0.03 nmol/mL to about 6 μmol/mL.

The acidic solution for use in the liquid preparation of the present invention is a solution of a carboxyl-containing compound. Example of the acidic solutions include acetic acid, lactic acid, citric acid, hydrochloric acid, propionic acid, butyric acid, benzoic acid, sulfuric acid, nitric acid, boric acid, carbonic acid, bicarbonic acid, gluconic acid, succinic acid, fumaric acid, maleic acid, methanesulfonic acid, malic acid, trifluoroacetic acid and salts thereof. The acidic solution may contain one or a combination of two or more selected from the group consisting of the salts of these acids. Preferably, the acidic solution contains one or a combination of two or more selected from the group consisting of acetic acid, lactic acid, phosphoric acid, glycine, citric acid, hydrochloric acid, propionic acid, butyric acid, benzoic acid and salts thereof. More preferably, the acidic solution contains one or a combination of two or more selected from the group consisting of acetic acid, lactic acid, propionic acid, butyric acid and/or phosphoric acid, and salts thereof.

The concentration of the acidic solution may be any concentration that can increase the BA of ghrelin: It is preferably in the range of 1 mM to 1000 mM and more preferably in the range of 10 mM to 500 mM.

It is preferred that the change in the pH of the aqueous solution is kept as small as possible in order to ensure stability of ghrelins during storage. To this end, a buffer can be used. The buffer preferably has a pH in the range of 3.0 to 7.0. Although the pH of the liquid preparation is stabilized following the addition of the buffer, the pH may vary by about 0.1 to about 0.2 due to the concentration of the used buffer or under specific conditions. Such variation is also encompassed by the present invention.

Specific examples of the buffer for use in the present invention include acetic acid buffer (including sodium acetate buffer and ammonium acetate buffer), lactic acid buffer, phosphoric acid buffer (including sodium phosphate buffer), glycine hydrochloride buffer, citric acid buffer (including sodium citrate buffer), citric acid-phosphoric acid buffer (including Mcilvaine buffer), phosphoric acid-acetic acid-boric acid buffer (including Britton-Robinson buffer), phthalic acid buffer and propionic acid buffer. These buffers may be used either individually or in combination. Acetic acid buffer, butyric acid buffer, propionic acid buffer, lactic acid buffer and/or phosphoric acid buffer are particularly suitable for use in the present invention.

The liquid preparation preferably has a pH in the range of 3.0 to 7.0 and more preferably in the range of 4.0 to 7.0. Although the liquid preparation with a pH less than 3.0 can increase the BA of ghrelin, it can cause pain especially when used as an injection and is undesirable.

In addition to the above-described buffer, a pH adjuster may be used to adjust the pH of the liquid preparation of the present invention. Examples of the pH adjuster include hydrochloric acid, sulfuric acid, nitric acid, boric acid, carbonic acid, bicarbonic acid, gluconic acid, sodium hydroxide, potassium hydroxide, aqueous ammonia, citric acid, monoethanolamine, lactic acid, acetic acid, succinic acid, fumaric acid, maleic acid, phosphoric acid, methanesulfonic acid, malic acid, propionic acid, trifluoroacetic acid and salts thereof.

In addition to the pH adjuster, a polar organic liquid may be used in the present invention. The addition of the polar organic liquid serves to increase the BA of subcutaneously injected ghrelin more than the acidic solution alone would. It is our finding that the addition of a polar organic liquid, such as an alcohol, to the liquid preparation of the present invention can increase the BA of ghrelin or modulate the absorption pattern of ghrelin.

Injections must be sterile. A preservative or a sterilizer may be added to an injection especially when the injection is used in multiple uses. Examples of the additive used for this purpose include benzyl alcohol, chlorobutanol, phenol and paraoxybenzoates.

Since administration of injections is often accompanied by pain, an injection may contain a pain-reliever to alleviate the pain. Examples of the additive used for this purpose include benzyl alcohol, chlorobutanol, phenol and local anesthetics such as procaine and xylocalne.

Patent Document 4 describes an injection that contains, in addition to an active ingredient, benzyl alcohol or its analogue as a pain-reliever, and cyclodextrin. Benzyl alcohol is used to reduce the pain associated with injection. Benzyl alcohol or its analogue is used to prevent hemolysis caused by benzyl alcohol.

Alcohols are often used as preservatives, sterilizers or pain-relievers. The present inventors have found that alcohols and other polar organic liquids enhance the ability of the acidic solution to increase the BA of ghrelin in the liquid preparation. No previous studies have reported this unique phenomenon.

Examples of the alcohol for use in the present invention include benzyl alcohol, chlorobutanol, phenol, methanol, ethanol, propanol, butanol, isopropanol, 2-butanol, isobutanol, cresol, m-cresol, chlorocresol, paraoxybenzoates (such as methylparaben and ethylparaben), inositol, propylene glycol, butylene glycol, cetanol, stearyl alcohol, hexyldecanol, hexanetriol, behenyl alcohol, lauryl alcohol, lanolin alcohol, glycerol (glycerin), ethylene glycol, diethylene glycol, diethylene glycol monobutyl ether, diethylene glycol monomethyl ether, menthol, borneol, maltol, ethylmaltol, eugenol, geraniol, thymol, diisopropanolamine, diethanolamine and trometamol. Benzyl alcohol, ethanol, phenol, tert-butanol and chlorobutanol are particularly suitable for use in the present invention.

Aside from alcohols, certain polar organic liquids, such as N-methyl-2-pyrrolidone, dimethylformamide, dimethylsulfoxide and methylparaben, also serve to increase the BA of ghrelin.

These polar organic liquids may be used either individually or in combination. The polar organic liquid may be used in any amount that provides its intended effect and that does not pose any problems during production and long term storage of the drugs of the present invention. The amount of the polar organic liquid is such that when the liquid preparation is formed into a solution for administration, the concentration of the polar organic liquid in the solution is typically in the range of 0.001 to 80% (w/v) and preferably in the range of 0.1 to 20% (w/v).

Other additives may also be added to the liquid preparation of the present invention depending on the desired purpose. Among such additives are isotonic agents, such as sodium chloride and mannitol, sterilizers, such as sodium benzoate, antioxidants, such as sodium bisulfite, sodium pyrosulfite and ascorbic acid, and pain-relievers, such as lidocaine hydrochloride and meprylcaine hydrochloride.

As described, the present invention provides a liquid preparation that contains as an active ingredient a physiologically active peptide or protein, including ghrelins, and that ensures high BA. Additives may be added to the liquid preparation to provide properties required for each preparation. For example, certain additives are added to injections to provide optimum osmotic pressure, optimum solubility, low irritancy, high sterilizing effect and adsorption prevention.

The liquid preparation in accordance with the present invention is intended for parenteral administration. Specifically, it is intended for injection, infusion and nasal administration. While the present invention can be applied to different types of injection, including intravenous injection, subcutaneous injection, intracutaneous injection, intramuscular injection and intravenous drip infusion, the increase in the BA is most significant in subcutaneous injection and intramuscular injection.

The liquid preparation of the present invention can be produced by processes commonly used in the production of pharmaceutical products. In one exemplary process, a freeze dried product of a physiologically active peptide or protein, including ghrelins, is dissolved in purified water to form a drug solution. Meanwhile, a buffer and other additives are dissolved in purified water to form an additive solution. The drug solution and the additive solution are mixed together and the mixture is processed as required (e.g., sterilization and filtration). The processed mixture is sealed in ampoules or vials to obtain a finished product of ghrelin preparation.

Injections are often provided in the form of a preparation that is formed into a solution upon use. This type of preparation is desirable when it is difficult to maintain the stability of active ingredients in the form of a solution. The present invention also encompasses the dissolved-upon-use preparation that can be formed into a liquid preparation containing as an active ingredient a physiologically active peptide or protein, including ghrelins. The dissolved-upon-use preparation can be produced by either of the following two procedures: The above-described additives are properly selected and added in desired amounts to a solid ghrelin product, such as powdered ghrelin, to form a solid composition, or the above-described additives are properly selected and added in desired amounts to an aqueous solution of ghrelins to form a liquid composition, which in turn is dried to make a solid composition. Upon use, these solid compositions are dissolved in a solvent such as water to form a liquid preparation. Solvents other than water, such as ethanol and 2-propanol, may also be used in pharmaceutically acceptable amounts.

A sugar may also be added to the preparation of the present invention when the physiologically active peptide or protein, including ghrelins, is provided in the form of a solid composition. We have found that, when used in conjunction with the acidic solution and/or the polar organic liquid, the sugar serves to further increase the BA of the physiologically active peptide or protein, including ghrelins.

Examples of the sugar for use in the present invention include monosaccharides, such as mannitol, glucose, fructose, inositol, sorbitol and xylitol; disaccharides, such as sucrose, lactose, maltose and trehalose; polysaccharides, such as starch, dextran, pullulan, alginic acid, hyaluronic acid, pectic acid, phytic acid, phytin, chitin and chitosan; dextrins, such as α-cyclodextrin, β-cyclodextrin, γ-cyclodextrin, dextrin, hydroxypropyl starch and hydroxyethyl starch; and celluloses, such as methyl cellulose, ethyl cellulose, hydroxyethyl cellulose, hydroxypropyl cellulose, hydroxypropylmethyl cellulose and carboxymethylcellulose sodium. These sugars may be used either individually or in combination.

Of these sugars, mannitol, sucrose, glucose and cyclodextrin are particularly preferred for use in the present invention with cyclodextrin being most preferred.

It has been reported that, of different cyclodextrins, sulfobutylether β-cyclodextrin derivatives (β-CyDs) act to increase the BA of insulin subcutaneously injected in rats (Non-Patent Document 2).

It is well-known that when added to pharmaceutical products, cyclodextrins improve the solubility of less water-soluble compounds and the storage stability of the pharmaceutical products.

Patent Document 6 describes a preparation containing an interferon polypeptide and sulfoalkylether cyclodextrin. In this preparation, the sulfoalkylether cyclodextrin derivative serves as a stabilizer of the composition and helps maintain the biological activity of the interferon polypeptide.

Patent Document 7 describes a nasal preparation containing a physiologically active polypeptide and cyclodextrin while Patent Document 8 describes a vaginal preparation containing a physiologically active polypeptide and cyclodextrin. The nasal preparation and the vaginal preparation are each developed as a non-injection preparation that facilitates the mucosal absorption of the physiologically active polypeptide, which otherwise is hydrolyzed by enzymes present in the gastrointestinal lumen or wall. In these preparations, cyclodextrin acts to facilitate the absorption of physiologically active polypeptides.

Patent Document 9 describes a method for solubilizing and stabilizing interferon and other proteins with the help of β- and γ-cyclodextrins. However, none of these literatures suggest or disclose the present invention to increase the BA of subcutaneously injected physiologically active peptides or proteins.

These sugars can be used either individually or in combination. The sugar may be used in any amount that provides its intended effect, that does not pose any problems during production and long term storage of the drug, and that provides the liquid preparation with a proper viscosity that does not pose any problems during production and administration of the liquid preparation. For example, the amount of the sugar is such that when the liquid preparation is formed into a solution for administration, the concentration of the sugar in the solution is in the range of 0.1 to 20% (w/v).

As set forth, the present invention demonstrates that the addition of an acidic solution, a polar organic liquid or a sugar to a liquid preparation containing a physiologically active peptide or protein can significantly increase the BA of the peptide or protein even when the preparation is subcutaneously injected. Examples of the physiologically active peptide or protein for use in the present invention include ghrelin and derivatives and analogues thereof, human glucagon-like peptide-1 (hGLP-1), human atrial natriuretic peptide (hANP), human adrenomedulin, human parathyroid hormone (hPTH(1-34)) and human insulin. The present invention offers a new way of subcutaneously administering physiologically active peptides or proteins, such as ghrelins, that otherwise cannot be subcutaneously administered to achieve pharmaceutically effective plasma levels.

EXAMPLES

The present invention will now be described in further detail with reference to examples, which are not intended to limit the scope of the invention in any way.

Abbreviations used in the following Examples have meanings as described below. Unless otherwise specified, the following methods and instruments were used in the testing.
[Instruments Used]
(A) pH measurement
Instrument: CASTANY LAB pH meter F-22, Horiba Ltd.
(B) Radioimmunoassay (RIA)
Instrument: γ-counter COBRA-II, Packard Instruments Co., Ltd.
(C) Enzyme-Linked Immunosolvent Assay (ELISA)
Instrument: Microplate reader, Molecular Devices Corp.

Comparative Example 1

Preparation of Preparations Containing Human Ghrelin (1)

Human ghrelin was dissolved in a 5% (w/v) aqueous mannitol solution, physiological saline or a 10% (w/v) aqueous sucrose solution at different concentrations as shown in Table 2 below to make Preparations No. 1 through 5 and No. 34 and 35.

TABLE 2

| Preparation No | Solutions | Concentration of human ghrelin |
|---|---|---|
| 1 | 5%(w/v) Aqueous mannitol solution | 5 μg/mL |
| 2 | 5%(w/v) Aqueous mannitol solution | 20 μg/mL |
| 3 | 5%(w/v) Aqueous mannitol solution | 50 μg/mL |
| 4 | 5%(w/v) Aqueous mannitol solution | 1,000 μg/mL |
| 5 | 5%(w/v) Aqueous mannitol solution | 2,000 μg/mL |
| 34 | Physiological saline | 50 μg/mL |
| 35 | 10%(w/v) Aqueous sucrose solution | 50 μg/mL |

Example 1

Preparation of Preparations Containing Human Ghrelin (2)

The following buffers were prepared as described below: 0.5M sodium acetate buffer, 0.5M ammonium acetate buffer, 0.5M acetic acid buffer, 0.5M sodium phosphate buffer, 0.5M citric acid buffer, 0.5M glycine hydrochloride buffer, 1M lactic acid buffer, 0.06M propionic acid buffer and 0.06M n-butyric acid buffer. The pH of each buffer is shown in the parenthesis.

(1) 0.5M Sodium Acetate Buffer (pH 7.0)
Purified water was added to 8.20 g sodium acetate (MW=82.03) to a volume of 100 mL. To this solution, 1M hydrochloric acid was added to a pH of 7.0. Purified water was further added to a final volume of 200 mL.

(2) 0.5M Sodium Acetate Buffer (pH 4.0)
Purified water was added to 8.20 g sodium acetate (MW=82.03) to a volume of 100 mL. To this solution, 1M hydrochloric acid was added to a pH of 4.0. Purified water was further added to a final volume of 200 mL.

(3) 0.5M Sodium Acetate Buffer (pH 5.0)
Purified water was added to 8.20 g sodium acetate (MW=82.03) to a volume of 100 mL. To this solution, 1M hydrochloric acid was added to a pH of 5.0. Purified water was further added to a final volume of 200 mL.

(4) 0.5M Sodium Acetate Buffer (pH 6.0)
Purified water was added to 8.20 g sodium acetate (MW=82.03) to a volume of 100 mL. To this solution, 1M hydrochloric acid was added to a pH of 6.0. Purified water was further added to a final volume of 200 mL.

(5) 0.5M Ammonium Acetate Buffer (pH 4.0)
Purified water was added to 7.71 g ammonium acetate (MW=77.08) to a volume of 100 mL. To this solution, 1M hydrochloric acid was added to a pH of 4.0. Purified water was further added to a final volume of 200 mL.

(6) 0.5M Acetic Acid Buffer (pH 4.0)
Purified water was added to 6.01 g acetic acid (MW=60.05) to a volume of 100 mL. To this solution, 1M sodium hydroxide was added to a pH of 4.0. Purified water was further added to a final volume of 200 mL.

(7) 0.5M Sodium Phosphate Buffer (pH 4.0)
Purified water was added to 15.60 g sodium dihydrogen phosphate dihydrate (MW=156.01) to a volume of 100 mL. To this solution, 1M hydrochloric acid was added to a pH of 4.0. Purified water was further added to a final volume of 200 mL.

(8) 0.5M Sodium Phosphate Buffer (pH 5.0)

Purified water was added to 15.60 g sodium dihydrogen phosphate dihydrate (MW=156.01) to a volume of 100 mL. To this solution, 1M sodium hydroxide was added to a pH of 5.0. Purified water was further added to a final volume of 200 mL.

(9) 0.5M Citric Acid Buffer (pH 4.0)

Purified water was added to 10.51 g citric acid monohydrate (MW=210.14) to make 100 mL aqueous citric acid. Meanwhile, purified water was added to 14.71 g trisodium citrate (MW=294.10) to make a 100 mL solution of trisodium citrate. The aqueous citric acid and the aqueous trisodium citrate solution were mixed together to obtain the desired buffer with a pH of 4.0.

(10) 0.5M Glycine Hydrochloride Buffer (pH 4.0)

Purified water was added to 7.51 g glycine (MW=75.07) to a volume of 100 mL. To this solution, 1M hydrochloric acid was added to a pH of 4.0. Purified water was further added to a final volume of 200 mL.

(11) 1M Lactic Acid Buffer (pH 4.0)

Purified water was added to 45.04 g lactic acid (MW=90.08) to a volume of 250 mL. To this solution, 1M sodium hydroxide was added to a pH of 4.0. Purified water was further added to a final volume of 500 mL.

(12) 0.06M Propionic Acid Buffer (pH 4.0)

Purified water was added to 2.22 g propionic acid (MW=74.08) to a volume of 250 mL. To this solution, 1M sodium hydroxide was added to a pH of 4.0. Purified water was further added to a final volume of 500 mL.

(13) 0.06M N-Butyric Acid Buffer (pH 4.0)

Purified water was added to 2.64 g butyric acid (MW=88.11) to a volume of 250 mL. To this solution, 1M sodium hydroxide was added to a pH of 4.0. Purified water was further added to a final volume of 500 mL.

These buffers or solutions obtained by diluting the buffers were used as acidic solutions. The acidic solutions, human ghrelin and optional additives were mixed together to make Preparations No. 6 through 33, No. 51 through 59, No. 73, and No. 81 through 97, containing human ghrelin at concentrations shown in Table 3.

TABLE 3

| Prep. No | Acidic solutions (pH) | Conc. of human ghrelin | Additives |
|---|---|---|---|
| 6 | 0.5M Sodium acetate buffer (7.0) | 50 | None |
| 7 | 0.5M Sodium acetate buffer (4.0) | 50 | None |
| 8 | 0.5M Ammonium acetate buffer (4.0) | 50 | None |
| 9 | 0.5M Citric acid buffer (4.0) | 50 | None |
| 10 | 0.5M Glycine/hydrochloric acid buffer (4.0) | 50 | None |
| 11 | 0.5M Sodium phosphate buffer (4.0) | 50 | None |
| 12 | 0.5M Sodium acetate buffer (4.0) | 50 | 10%(w/v) Sucrose |
| 13 | 0.1M Sodium acetate buffer (4.0) | 50 | 10%(w/v) Sucrose |
| 14 | 0.03M Sodium acetate buffer (4.0) | 50 | 10%(w/v) Sucrose |
| 15 | 0.01M Sodium acetate buffer (4.0) | 50 | 10%(w/v) Sucrose |
| 16 | 0.1M Sodium acetate buffer (5.0) | 50 | 10%(w/v) Sucrose |
| 17 | 0.1M Sodium acetate buffer (6.0) | 50 | 10%(w/v) Sucrose |
| 18 | 0.5M Sodium phosphate buffer (4.0) | 50 | 10%(w/v) Sucrose |
| 19 | 0.25M Sodium phosphate buffer (4.0) | 50 | 10%(w/v) Sucrose |
| 20 | 0.1M Sodium phosphate buffer (4.0) | 50 | 10%(w/v) Sucrose |
| 21 | 0.5M Sodium phosphate buffer (5.0) | 50 | 10%(w/v) Sucrose |
| 22 | 0.25M Sodium phosphate buffer (5.0) | 50 | 10%(w/v) Sucrose |
| 23 | 0.1M Sodium phosphate buffer (5.0) | 50 | 10%(w/v) Sucrose |
| 24 | 0.1M Sodium acetate buffer (4.0) | 50 | None |
| 25 | 0.1M Sodium acetate buffer (4.0) | 50 | 20%(w/v) Sucrose |
| 26 | 0.1M Sodium acetate buffer (4.0) | 10 | 10%(w/v) Sucrose |
| 27 | 0.1M Sodium acetate buffer (4.0) | 250 | 10%(w/v) Sucrose |
| 28 | 0.1M Sodium acetate buffer (4.0) | 2000 | 10%(w/v) Sucrose |
| 29 | 0.1M Sodium acetate buffer (4.0) | 50 | 10%(w/v) Sucrose/ 1%(w/v) Benzyl alcohol |
| 30 | 0.03M Sodium acetate buffer (4.0) | 50 | 10%(w/v) Sucrose/ 1%(w/v) Benzyl alcohol |
| 31 | 0.03M Sodium acetate buffer (4.0) | 1000 | 10%(w/v) Sucrose/ 1%(w/v) Benzyl alcohol |
| 32 | 0.03M Acetic acid buffer (4.0) | 1000 | 10%(w/v) Sucrose/ 1%(w/v) Benzyl alcohol |
| 33 | 0.03M Sodium acetate buffer (4.0) | 2000 | 10%(w/v) Sucrose/ 1%(w/v) Benzyl alcohol |
| 55 | 0.03M Lactic acid buffer (4.0) | 50 | 10%(w/v) Sucrose/ 1%(w/v) Benzyl alcohol |
| 56 | 0.1M Lactic acid buffer (4.0) | 50 | 10%(w/v) Sucrose/ 1%(w/v) Benzyl alcohol |
| 57 | 0.5M Lactic acid buffer (4.0) | 50 | 10%(w/v) Sucrose/ 1%(w/v) Benzyl alcohol |
| 58 | 0.03M Propionic acid buffer (4.0) | 50 | 10%(w/v) Sucrose/ 1%(w/v) Benzyl alcohol |
| 59 | 0.03M n-butyric acid buffer (4.0) | 50 | 10%(w/v) Sucrose/ 1% (w/v) Benzyl alcohol |
| 73 | 16 mM Benzoic acid | 50 | 10%(w/v) Sucrose/ |
| 81 | 0.03M Acetic acid buffer (4.0) | 50 | 10%(w/v) Sucrose/ 0.1%(w/v) Benzyl alcohol |
| 82 | 0.03M Acetic acid buffer (4.0) | 50 | 10%(w/v) Sucrose/ 3%(w/v) Benzyl alcohol |

TABLE 3-continued

| Prep. No | Acidic solutions (pH) | Conc. of human ghrelin | Additives |
|---|---|---|---|
| 83 | 0.03M Acetic acid buffer (4.0) | 50 | 10%(w/v) Sucrose/ 1%(w/v) Benzyl alcohol/ 10%(w/v) N-methyl-2-pyrrolidone |
| 84 | 0.03M Acetic acid buffer (4.0) | 50 | 10%(w/v) Glucose/ 1%(w/v) Benzyl alcohol |
| 85 | 0.03M Acetic acid buffer (4.0) | 50 | 10%(w/v) Dextran 70/ 1%(w/v) Benzyl alcohol |
| 86 | 0.03M Acetic acid buffer (4.0) | 50 | 10%(w/v) Sucrose/ 0.5%(w/v) Chlorobutanol |
| 87 | 0.25M Sodium phosphate buffer (4.0) | 50 | 10%(w/v) Sulfobutyl ether-β-cyclodextrin sodium salt (Trade Name: Captizol) |
| 88 | 0.01M Sodium acetate buffer (4.0) | 50 | 10%(w/v) Sulfobutyl ether-β-cyclodextrin sodium salt (Trade Name: Captizol) |
| 89 | 0.1M Sodium acetate buffer (4.0) | 50 | 1%(w/v) Sulfobutyl ether-β-cyclodextrin sodium salt (Trade Name: Captizol) |
| 90 | 0.1M Sodium acetate buffer (4.0) | 50 | 1%(w/v) 2-hydroxypropyl-β-cyclodextrin |
| 91 | 0.1M Sodium acetate buffer (4.0) | 1000 | 1%(w/v) Sulfobutyl ether-β-cyclodextrin sodium salt (Trade Name: Captizol) |
| 92 | 0.1M Sodium acetate buffer (4.0) | 1000 | 1%(w/v) Sulfobutyl ether-β-cyclodextrin sodium salt (Trade Name: Captizol) |
| 93 | 0.01M Sodium acetate buffer (4.0) | 1000 | 10%(w/v) Sulfobutyl ether-β-cyclodextrin sodium salt (Trade Name: Captizol) |
| 94 | 0.1M Sodium acetate buffer (4.0) | 1000 | 10%(w/v) Sulfobutyl ether-β-cyclodextrin sodium salt (Trade Name: Captizol) |
| 95 | 0.03M Sodium acetate buffer (4.0) | 1000 | 1%(w/v) Sulfobutyl ether-β-cyclodextrin sodium salt (Trade Name: Captizol)/ 10%(w/v) Sucrose |
| 96 | 0.03M Sodium acetate buffer (4.0) | 1000 | 4%(w/v) Sulfobutyl ether-β-cyclodextrin sodium salt (Trade Name: Captizol)/ 10%(w/v) Sucrose |
| 97 | 0.03M Acetic acid buffer (4.0) | 50 | 10%(w/v) Sulfobutyl ether-β-cyclodextrin sodium salt (Trade Name: Captizol)/ 1%(w/v) Benzyl alcohol |

The buffers above or solutions obtained by diluting the buffers were used as acidic solutions. The acidic solutions, different peptides and optional additives were mixed together to make Preparations No. 36 through 50 and No. 98 through 107, containing peptides at concentrations shown in Table 4.

TABLE 4

| Prep. No | Solutions | Types of peptide | Conc. of peptide |
|---|---|---|---|
| 36 | Physiological saline | Rat ghrelin | 20 μg/mL |
| 37 | 5%(w/v) Aqueous mannitol solution | Rat ghrelin | 50 μg/tnL |
| 38 | 5%(w/v) Aqueous mannitol solution | Human des-octanoyl ghrelin | 10 μg/mL |
| 39 | 5%(w/v) Aqueous mannitol solution | Human des-octanoyl ghrelin | 50 μg/mL |
| 40 | Physiological saline | Human[L-2-aminododecanoic acid$^3$]ghrelin | 20 μg/mL |
| 41 | 5%(w/v) Aqueous mannitol solution | Human[L-2-aminododecanoic acid$^3$]ghrelin | 50 μg/mL |
| 42 | Physiological saline | Human glucagon-like peptide-1 (hGLP-1) | 30 μg/mL |
| 43 | 5%(w/v) Aqueous mannitol solution | Human glucagon-like peptide-1 (hGLP-1) | 50 μg/mL |

TABLE 4-continued

| Prep. No | Solutions | Types of peptide | Conc. of peptide |
|---|---|---|---|
| 44 | 5%(w/v) Aqueous mannitol solution | Human atrial natriuretic peptide (hANP) | 100 μg/mL |
| 45 | 5%(w/v) Aqueous mannitol solution | Human atrial natriuretic peptide (hANP) | 100 μg/mL |
| 46 | 5%(w/v) Aqueous glucose solution | Human adrenomedullin | 75 μg/mL |
| 47 | 5%(w/v) Aqueous mannitol solution | Human adrenomedullin | 150 μg/mL |
| 48 | Physiological saline | Human parathyroid hormone(hPTH(1-34)) | 50 μg/mL |
| 49 | 5%(w/v) Aqueous mannitol solution | Human parathyroid hormone(hPTH(1-34)) | 50 μg/mL |
| 50 | 5%(w/v) Aqueous mannitol solution | Human insulin | 50 μg/mL |
| 98 | 0.03M Acetic acid buffer(4.0)/ 10%(w/v) Sucrose/ 1%(w/v) Benzyl alcohol | Rat ghrelin | 50 μg/mL |
| 99 | 0.03M Acetic acid buffer(4.0)/ 10%(w/v) Sucrose/ | Human des-octanoyl ghrelin | 50 μg/mL |
| 100 | 10%(w/v) Sucrose/ 1%(w/v) Benzyl alcohol | Human des-octanoyl ghrelin | 50 μg/mL |
| 101 | 0.03M Acetic acid buffer(4.0)/ 10%(w/v) Sucrose/ 1%(w/v) Benzyl alcohol | Human des-octanoyl ghrelin | 50 μg/mL |
| 102 | 0.03M Acetic acid buffer(4.0)/ 10%(w/v) Sucrose/ 1%(w/v) Benzyl alcohol | Human[L-2-aminododecanoic acid$^3$]ghrelin | 50 μg/mL |
| 103 | 0.03M Acetic acid buffer(4.0)/ 10%(w/v) Sucrose/ 1%(w/v) Benzyl alcohol | Human glucagon-like peptide-1 (hGLP-1) | 50 μg/mL |
| 104 | 0.03M Acetic acid buffer(4.0)/ 10%(w/v) Sucrose/ 1%(w/v) Benzyl alcohol | Human atrial natriuretic peptide (hANP) | 100 μg/mL |
| 105 | 0.03M Acetic acid buffer(4.0)/ 10%(w/v) Sucrose/ 1%(w/v) Benzyl alcohol | Human adrenomedullin | 150 μg/mL |
| 106 | 0.03M Acetic acid buffer(4.0)/ 10%(w/v) Sucrose/ 1%(w/v) Benzyl alcohol | Human parathyroid hormone(hPTH (1-34)) | 50 μg/mL |
| 107 | 0.03M Acetic acid buffer(4.0)/ 10%(w/v) Sucrose/ 1%(w/v) Benzyl alcohol | Human insulin | 50 μg/mL |

Human ghrelin and additives were mixed together without acidic solutions to make Preparations No. 60 through 68, No. 70 through 72, No. 74, No. 76, and No. 78 through No. 80.

TABLE 5

| Prep. No | Sugars | Concent. of human ghrelin (μg/mL) | Additives |
|---|---|---|---|
| 60 | 10%(w/v) Sucrose | 50 | 1%(w/v) Ethanol |
| 61 | 10%(w/v) Sucrose | 50 | 10%(w/v) Ethanol |
| 61 | 10%(w/v) Sucrose | 50 | 20%(w/v) Ethanol |
| 63 | 10%(w/v) Sucrose | 50 | 1%(w/v) tert-butanol |
| 64 | 10%(w/v) Sucrose | 50 | 1%(w/v) N-methyl-2-pyrrolidone |
| 65 | 10%(w/v) Sucrose | 50 | 10%(w/v) N-methyl-2-pyrrolidone |
| 66 | 10%(w/v) Sucrose | 50 | 20%(w/v) N-methyl-2-pyrrolidone |
| 67 | 10%(w/v) Sucrose | 50 | 10%(w/v) Dimethylformamide |
| 68 | 10%(w/v) Sucrose | 50 | 10%(w/v) Dimethylsulfoxide |
| 70 | 10%(w/v) Sucrose | 50 | 1%(w/v) Sodium dodecylsulfate(SDS) |
| 71 | 10%(w/v) Sucrose | 50 | 0.2%(w/v) Phenol |
| 72 | 10%(w/v) Sucrose | 50 | 1%(w/v) Phenol |
| 74 | 10%(w/v) Sucrose | 50 | 0.2%(w/v) Methylparaben |
| 76 | 10%(w/v) Sucrose | 50 | 1%(w/v) Propylene glycol |
| 78 | 10%(w/v) Sucrose | 50 | 0.1%(w/v) Benzyl alcohol |
| 79 | 10%(w/v) Sucrose | 50 | 1%(w/v) Benzyl alcohol |
| 80 | 5%(w/v) Mannitol | 50 | 1%(w/v) Benzyl alcohol |

Some of the pharmaceutical additives used in the above-described Preparations are listed in the Japanese Pharmacopoeia. All of these additives meet the standards specified in the Japanese Pharmacopoeia.

Comparative Example 2

Pharmacokinetics of Intravenously and Subcutaneously Injected Ghrelin in Rats

Preparations No. 2 and No. 3 obtained in Comparative Example 1 were intravenously and subcutaneously administered to rats and the plasma levels of ghrelin were measured.
7-week old, male SD rats (Charles River Laboratories Japan Inc.) were used. A group of three rats was used for the tests. For intravenous administration, these animals each inserted a polyethylene tube (PE-50, Clay Adams Co., Ltd.) in the femoral artery were used. Preparation No. 2 was administered through the tail vain at a dose of 0.5 mL/kg by using a syringe and a 26 G needle (each available from Terumo Co., Ltd.). Blood samples were collected from the polyethylene tube in the femoral artery before administration and 1, 3, 5, 10, 20, 30, 60, and 90 minutes after administration.

Similarly, these animals inserted a polyethylene tube in the femoral artery were used for subcutaneous administration of Preparation No. 3 in the dorsal skin at a dose of 1 mL/kg using a syringe and a 26 G needle. Blood samples were collected from the polyethylene tube in the femoral artery before administration and 5, 10, 20, and 30 minutes after administration.

To each sample, one-hundredth as much of an EDTA.2Na.2H$_2$O solution and one-fiftieth as much of an AEBSF solution were added immediately after collection of the sample. The sample was then centrifuged to separate plasma, to which one-tenth as much 1N hydrochloric acid was immediately added. The sample was mixed and stored at −80° C. until analysis.

The plasma samples were then analyzed for the ghrelin levels by radioimmunoassay (RIA) using an anti-ghrelin antibody. Specifically, the anti-ghrelin antibody and then [$^{1,25}$I-Tyr$^{29}$]ghrelin were added to each plasma sample for competition. Subsequently, a secondary antibody was added to precipitate the antibody-ghrelin complex. The supernatant was separated and analyzed for radioactivity by a γ-counter (Packard Instruments Co., Ltd.). Since the anti-ghrelin antibody used in the assay specifically recognizes ghrelin, but not des-acyl ghrelin (an inactive form of ghrelin that does not have an octanoyl group), the assay can specifically detect the active ghrelin.

FIG. 1 shows the changes in the plasma ghrelin concentrations over time. The results shown in FIG. 1 were used to determine the following pharmacokinetic parameters for each injection route: the maximum plasma ghrelin concentration ($C_{max}$) and the time it took before the maximum plasma concentration was reached (T). The concentration ($C_0$) at time 0 was extrapolated for intravenous administration. Using the trapezoidal method, the area under the concentration curve (AUC) was also calculated for each injection route. The AUCs were then used to determine the bioavailability (BA) of ghrelin. The results are shown in Table 6. These values were obtained as averages of the data obtained for the three rats in each group.

TABLE 6

Pharmacokinetic parameters of ghrelin preparations intravenously or subcutaneously administered to rats with a 5% aqueous mannitol solution

| Prepar. No. Route of administration | Dose volume (mL/kg) | $C_0$ or Cmax (ng/mL) | Tmax (min) | AUC (ng · min/mL) | BA (%) |
|---|---|---|---|---|---|
| 2 i.v. | 0.5 | 40.69 ± 4.28 | — | 205.98 ± 14.69 | — |
| 3 s.c. | 1 | 1.70 ± 0.69 | 6.67 ± 2.89 | 25.72 ± 9.50 | 2.5 ± 0.9 |

As can be seen from the results shown in Table 6, the AUC for the intravenous administration of Preparation No. 2 at a dose of 10 μg/kg was determined to be 205.98 ng·min/mL, whereas the AUC for the subcutaneous administration of Preparation No. 3 at a dose of 50 μg/kg was determined to be 25.72 ng·min/mL. Thus, the BA of human ghrelin dissolved in a 5% aqueous mannitol solution was determined to be 2.5%.

Example 2

Effects of Sodium Acetate Buffers on Pharmacokinetics of Subcutaneously Injected Ghrelin in Rats As in Comparative Example 2, Preparations No. 34, No. 6 and No. 7 were subcutaneously administered at a dose of 1 mL/kg and the plasma ghrelin levels were measured by RIA method. The results are shown in FIG. 2. The pharmacokinetic parameters are shown in Table 7 below.

TABLE 7

Pharmacokinetic parameters of ghrelin preparations subcutaneously administered to rats (Effects of sodium acetate buffer)

| Prepar. No. | Dose volume (mL/kg) | Cmax (ng/mL) | Tmax (min) | AUC (ng · min/mL) | BA (%) |
|---|---|---|---|---|---|
| 34 | 1 | 3.35 ± 1.28 | 5.00 ± 0.00 | 51.94 ± 21.60 | 5.0 ± 2.1 |
| 6 | 1 | 12.57 ± 1.62 | 5.00 ± 0.00 | 235.38 ± 22.59 | 22.9 ± 2.2 |
| 7 | 1 | 22.29 ± 8.97 | 8.33 ± 2.89 | 363.38 ± 16.64 | 35.3 ± 1.6 |

As can be seen from the results of Table 7, the BAs obtained for Preparations No. 6 and No. 7 were 22.9% and 35.3%, respectively. These were surprisingly high as compared to the BA for Preparation No. 34 with physiological saline (5.0%) and the BA for Preparation No. 3 with a 5% (w/v) aqueous mannitol solution (2.5%): Regardless of the pH of the 0.5M sodium acetate buffer, the BA of ghrelin was markedly increased by the addition of the sodium acetate buffer. With the sodium acetate buffer, the BA was 9 to 14 times higher than the BA obtained for the 5% (w/v) aqueous mannitol solution.

Example 3

Effects of the Type of Acid Solution on Pharmacokinetics of Subcutaneously Injected Ghrelin in Rats As in Comparative Example 2, Preparations No. 7, No. 8, No. 9, No. 10 and No. 11 were subcutaneously administered at a dose of 1 mL/kg and the plasma ghrelin levels were measured by RIA method. The pharmacokinetic parameters are shown in Table 8 below.

TABLE 8

Pharmacokinetic parameters of ghrelin preparations subcutaneously administered to rats (Effects of types of acid solution)

| Prepar. No. | Dose volume (mL/kg) | Cmax (ng/mL) | Tmax (min) | AUC (ng · min/mL) | BA (%) |
|---|---|---|---|---|---|
| 7  | 1 | 22.29 ± 8.97 | 8.33 ± 2.89  | 363.38 ± 16.64 | 35.3 ± 1.6 |
| 8  | 1 | 13.29 ± 4.74 | 6.67 ± 2.89  | 214.93 ± 41.01 | 20.9 ± 4.0 |
| 9  | 1 | 3.70 ± 1.09  | 13.33 ± 5.77 | 72.02 ± 10.33  | 7.0 ± 1.0  |
| 10 | 1 | 6.12 ± 3.60  | 6.67 ± 2.89  | 91.68 ± 76.60  | 8.9 ± 7.4  |
| 11 | 1 | 10.99 ± 5.40 | 5.00 ± 0.00  | 167.50 ± 61.11 | 16.3 ± 5.9 |

The BAs obtained for Preparations No. 7, No. 8, No. 9, No. 10 and No. 11 were 35.3%, 20.9%, 7.0%, 8.9% and 16.3%, respectively. Thus, the BA of ghrelin was markedly increased in any of the acidic buffer solutions, each having a pH of 4.0, as compared to the BA for the 5% (w/v) aqueous mannitol solution.

Example 4

Effects of the Concentration of Acid Solution on Pharmacokinetics of Subcutaneously Injected Ghrelin in Rats As in Comparative Example 2, Preparations No. 12, No. 13, No. 14 and No. 15 were subcutaneously administered at a dose of 1 mL/kg and the plasma ghrelin levels were measured by RIA method. The pharmacokinetic parameters are shown in Table 9 below.

TABLE 9

Pharmacokinetic parameters of ghrelin preparations subcutaneously administered to rats (Effects of the concentration of acid solution)

| Prepar. No. | Dose volume (mL/kg) | Cmax (ng/mL) | Tmax (min) | AUC (ng · min/mL) | BA (%) |
|---|---|---|---|---|---|
| 12 | 1 | 20.84 ± 6.82 | 5.00 ± 0.00 | 350.53 ± 51.36 | 34.0 ± 5.0 |
| 13 | 1 | 16.47 ± 2.82 | 6.67 ± 2.89 | 289.90 ± 57.30 | 28.1 ± 5.6 |
| 14 | 1 | 9.08 ± 2.76  | 6.67 ± 2.89 | 142.04 ± 32.17 | 13.8 ± 3.1 |
| 15 | 1 | 3.04 ± 0.85  | 5.00 ± 0.00 | 49.38 ± 15.82  | 4.8 ± 1.5  |

The BAs obtained for Preparations No. 12, No. 13, No. 14 and No. 15 were 34.0%, 28.1%, 13.8% and 4.8%, respectively. Thus, the BA of ghrelin was markedly increased in any of the acidic solutions (pH 4.0) and a sodium acetate concentration in the range of 0.01 M to 0.5 M, as compared to the BA for the 5% (w/v) aqueous mannitol solution.

Example 5

Effects of the pH of Liquid Preparation on Pharmacokinetics of Subcutaneously Injected Ghrelin in Rats As in Comparative Example 2, Preparations No. 13, No. 16 and No. 17 were subcutaneously administered at a dose of 1 mL/kg and the plasma ghrelin levels were measured by RIA method. The pharmacokinetic parameters are shown in Table 10 below.

TABLE 10

Pharmacokinetic parameters of ghrelin preparations subcutaneously administered to rats (Effects of the pH of liquid preparation)

| Prepar. No. | Dose volume (mL/kg) | Cmax (ng/mL) | Tmax (min) | AUC (ng · min/mL) | BA (%) |
|---|---|---|---|---|---|
| 13 | 1 | 16.47 ± 2.82 | 6.67 ± 2.89 | 289.90 ± 57.30 | 28.1 ± 5.6 |
| 16 | 1 | 9.49 ± 2.27 | 6.67 ± 2.89 | 170.56 ± 56.93 | 16.6 ± 5.5 |
| 17 | 1 | 5.59 ± 1.70 | 5.00 ± 0.00 | 93.23 ± 28.88 | 9.1 ± 2.8 |

The BAs obtained for Preparations No. 13, No. 16 and No. 17 were 28.1%, 16.6% and 9.1%, respectively. Thus, the BA of ghrelin was markedly increased in any of the liquid preparations, each formulated with a 0.1M sodium acetate solution serving as an acidic solution and having a pH in the range of 4.0 to 6.0, as compared to the BA for the 5% (w/v) aqueous mannitol solution.

Example 6

Effects of the Concentration and the pH of Phosphoric Acid Buffer on Pharmacokinetics of Subcutaneously Injected Ghrelin in Rats As in Comparative Example 2, Preparations No 18, No. 19, No. 20, No. 21, No. 22 and No. 23 were subcutaneously administered at a dose of 1 mL/kg and the plasma ghrelin levels were measured by RIA method.

The pharmacokinetic parameters are shown in Table 11 below.

TABLE 11

Pharmacokinetic parameters of ghrelin preparations subcutaneously administered to rats (Effects of the concentration and the pH of phosphoric acid buffer)

| Prepar. No. | Dose volume (mL/kg) | Cmax (ng/mL) | Tmax (min) | AUC (ng · min/mL) | BA (%) |
|---|---|---|---|---|---|
| 18 | 1 | 8.38 ± 1.45 | 11.67 ± 7.64 | 182.55 ± 22.06 | 17.7 ± 2.1 |
| 19 | 1 | 5.00 ± 0.91 | 8.33 ± 2.89 | 82.65 ± 2.78 | 8.0 ± 0.3 |
| 20 | 1 | 3.36 ± 1.66 | 5.00 ± 0.00 | 54.11 ± 25.62 | 5.3 ± 2.5 |
| 21 | 1 | 8.74 ± 0.31 | 6.67 ± 2.89 | 154.73 ± 19.02 | 15.0 ± 1.8 |
| 22 | 1 | 6.68 ± 3.01 | 8.33 ± 2.89 | 109.58 ± 52.62 | 10.6 ± 5.1 |
| 23 | 1 | 3.16 ± 1.26 | 6.67 ± 2.89 | 55.23 ± 28.90 | 5.4 ± 2.8 |

The BAs obtained for Preparations No. 18, No. 19, No. 20, No. 21, No. 22 and No. 23 were 17.7%, 8.0%, 5.3%, 15.0%, 10.6% and 5.4%, respectively. Thus, the BA of ghrelin was markedly increased in any of the liquid preparations, each formulated with a phosphoric acid buffer (pH 4.0 to 5.0), as compared to the BA for the 5% (w/v) aqueous mannitol solution.

Example 7

Effects of the Type and the Concentration of Alcohol on Pharmacokinetics of Subcutaneously Injected Ghrelin in Rats As in Comparative Example 2, Preparations No. 14, No. 30, No. 81, No. 82 and No. 86 were subcutaneously administered at a dose of 1 mL/kg and the plasma ghrelin levels were measured by RIA method.

The pharmacokinetic parameters are shown in Table 12 below.

TABLE 12

Pharmacokinetic parameters of ghrelin preparations subcutaneously administered to rats (Effects of the type and the concentration of alcohol)

| Prepar. No. | Dose volume (mL/kg) | Cmax (ng/mL) | Tmax (min) | AUC (ng · min/mL) | BA (%) |
|---|---|---|---|---|---|
| 14 | 1 | 9.08 ± 2.76 | 6.67 ± 2.89 | 142.04 ± 32.17 | 13.8 ± 3.1 |
| 30 | 1 | 15.99 ± 3.66 | 5.00 ± 0.00 | 259.89 ± 43.08 | 25.2 ± 4.2 |
| 81 | 1 | 13.94 ± 5.21 | 10.00 ± 0.00 | 265.31 ± 104.94 | 25.8 ± 10.2 |
| 82 | 1 | 11.77 ± 5.13 | 5.00 ± 0.00 | 141.91 ± 46.62 | 13.8 ± 4.5 |
| 86 | 1 | 14.30 ± 1.50 | 6.67 ± 2.89 | 231.96 ± 43.06 | 22.5 ± 4.2 |

The BAs obtained for Preparations No. 14, No. 30, No. 81, No. 82 and No. 86 were 13.8%, 25.2%, 25.8%, 13.8% and 22.5%, respectively. Preparation No. 14 contained an acidic solution and a sugar, but not any alcohols. Preparation No. 30 contained the same acidic solution and sugar as in Preparation No. 14 and further contains benzyl alcohol. The BA of ghrelin in Preparation No. 30 was twice as high as that in the alcohol-free Preparation No. 14. It was also demonstrated that the presence of an alcohol results in an increase in the BA of ghrelin regardless of the type and the concentration of the alcohol.

Example 8

Effects of the Concentration of Sucrose on Pharmacokinetics of Subcutaneously Injected Ghrelin in Rats As in Comparative Example 2, Preparations No. 24, No. 13 and No. 25 were subcutaneously administered at a dose of 1 mL/kg and the plasma ghrelin levels were measured by RIA method. The results were shown in FIG. 3 and the pharmacokinetic parameters are shown in Table 13 below.

TABLE 13

Pharmacokinetic parameters of ghrelin preparations subcutaneously administered to rats (Effects of the concentration of sucrose)

| Prepar. No. | Dose volume (mL/kg) | Cmax (ng/mL) | Tmax (min) | AUC (ng · min/mL) | BA (%) | T½ (min) |
|---|---|---|---|---|---|---|
| 24 | 1 | 22.15 ± 2.10 | 8.33 ± 2.89 | 393.84 ± 62.46 | 38.2 ± 6.1 | 9.74 ± 1.65 |
| 13 | 1 | 16.47 ± 2.82 | 6.67 ± 2.89 | 289.90 ± 57.30 | 28.1 ± 5.6 | 13.11 ± 1.85 |
| 25 | 1 | 8.99 ± 0.86 | 7.50 ± 3.54 | 199.76 ± 6.67 | 19.4 ± 0.6 | 27.47 ± 15.69 |

The BAs obtained for Preparations No. 24, No. 13 and No. 25 were 38.2%, 28.1% and 19.4%, respectively. Thus, the BA of ghrelin was markedly higher in any of the liquid preparations that contain the sodium acetate buffer serving as an acidic solution and 0, 10 or 20% (w/v) sucrose than in the 5% (w/v) aqueous mannitol solution. The presence of sucrose resulted in a increase in the T1/2 of ghrelin in Preparations No. 13 and No. 25 than in the sucrose-free Preparation No. 24.

Example 9

Effects of the Type of Sugar on Pharmacokinetics of Subcutaneously Injected Ghrelin in Rats As in Comparative Example 2, Preparations No. 35, No. 53, No. 84 and No. 85 were subcutaneously administered at a dose of 1 mL/kg and the plasma ghrelin levels were measured by RIA method. The pharmacokinetic parameters are shown in Table 14 below.

TABLE 14

Pharmacokinetic parameters of ghrelin preparations subcutaneously administered to rats (Effects of the type of sugar)

| Prepar. No. | Dose volume (mL/kg) | Cmax (ng/mL) | Tmax (min) | AUC (ng · min/mL) | BA (%) |
|---|---|---|---|---|---|
| 35 | 1 | 1.82 ± 0.20 | 5.00 ± 0.00 | 30.49 ± 5.03 | 3.0 ± 0.5 |
| 53 | 1 | 13.59 ± 3.72 | 5.00 ± 0.00 | 230.71 ± 43.38 | 22.4 ± 4.2 |
| 84 | 1 | 14.45 ± 2.88 | 5.00 ± 0.00 | 219.06 ± 23.27 | 21.3 ± 2.3 |
| 85 | 1 | 5.49 ± 3.66 | 6.67 ± 2.89 | 89.38 ± 53.97 | 8.7 ± 5.2 |

The BAs obtained for Preparations No. 35, No. 53, No. 84 and No. 85 were 3.0%, 22.4%, 21.3% and 8.7%, respectively. Although the BA of ghrelin was increased in Preparation No. 35 containing only sucrose, the increase was relatively small (3.0%). It was demonstrated that the BA of ghrelin was markedly increased in any of the liquid preparations that contained the same acidic solution and the same alcohol, but different sugars, as compared to the BA for the 5% (w/v) aqueous mannitol solution. The increase in the BA was higher for sucrose and glucose than for dextran 70.

Example 10

Effects of Cyclodextrin on Pharmacokinetics of Subcutaneously Injected Ghrelin in Rats As in Comparative Example 2, Preparations No. 87 through No. 97 were subcutaneously administered at a dose of 1 mL/kg and the plasma ghrelin levels were measured by RIA method.

The pharmacokinetic parameters are shown in Table 15 below.

TABLE 15

Pharmacokinetic parameters of ghrelin preparations subcutaneously administered to rats (Effects of cyclodextrin as sugar)

| Prepar. No. | Dose volume (mL/kg) | Cmax (ng/mL) | Tmax (min) | AUC (ng · min/mL) | BA (%) |
|---|---|---|---|---|---|
| 87 | 1 | 10.87 ± 2.07 | 23.33 ± 5.77 | 257.40 ± 34.41 | 25.0 ± 3.3 |
| 88 | 1 | 8.29 ± 1.10 | 10.00 ± 0.00 | 356.44 ± 11.79 | 34.6 ± 1.1 |
| 89 | 1 | 18.64 ± 1.79 | 10.00 ± 0.00 | 857.01 ± 253.30 | 83.2 ± 24.6 |
| 90 | 1 | 18.82 ± 4.04 | 10.00 ± 0.00 | 861.52 ± 176.63 | 83.6 ± 17.1 |
| 91 | 0.05 | 7.79 ± 2.63 | 8.33 ± 2.89 | 185.26 ± 61.90 | 18.0 ± 6.0 |
| 92 | 0.05 | 27.69 ± 7.03 | 8.33 ± 2.89 | 671.73 ± 122.02 | 65.2 ± 11.8 |
| 93 | 0.05 | 11.79 ± 7.41 | 25.00 ± 30.41 | 650.88 ± 242.71 | 63.2 ± 23.6 |
| 94 | 0.05 | 17.21 ± 8.52 | 25.00 ± 30.41 | 977.79 ± 208.78 | 94.9 ± 20.3 |
| 95 | 0.05 | 11.25 ± 4.79 | 6.67 ± 2.89 | 242.38 ± 116.53 | 23.5 ± 11.3 |
| 96 | 0.05 | 19.65 ± 3.04 | 5.00 ± 0.00 | 511.84 ± 66.67 | 49.7 ± 6.5 |
| 97 | 1 | 11.87 ± 1.34 | 40.00 ± 17.32 | 1078.71 ± 86.68 | 104.7 ± 8.4 |

The BA was markedly increased in any of Preparations No 87 through No. 97. The BAs of ghrelin in the sucrose-containing Preparation No. 53 and in the glucose-containing Preparation No. 84 were 22.4% and 21.3%, respectively. The increase in the BA of ghrelin was comparably high in any of the liquid preparations using cyclodextrin.

Example 11

Effects of the Dose of Ghrelin on Pharmacokinetics of Subcutaneously Injected Ghrelin in Rats As in Comparative Example 2, Preparations No. 26, No. 13, No. 27 and No. 28 were subcutaneously administered at a dose of 1 mL/kg. Doses of ghrelin delivered by these liquid preparations were 10, 50, 250 and 2,000 µg/kg, respectively. The blood samples were collected in the same manner as in Example 2 and the plasma ghrelin levels were measured by RIA method. The results are shown in FIGS. 4 and 5. The pharmacokinetic parameters are shown in Table 16 below.

TABLE 16

Pharmacokinetic parameters of ghrelin preparations
subcutaneously administered to rats (Effects of dose of ghrelin)

| Prepar. No. | Dose volume (mL/kg) | Cmax (ng/mL) | Tmax (min) | AUC (ng · min/mL) | BA (%) |
|---|---|---|---|---|---|
| 26 | 1 | 2.41 ± 0.18 | 10.00 ± 0.00 | 49.28 ± 4.04 | 23.9 ± 2.0 |
| 13 | 1 | 16.47 ± 2.82 | 6.67 ± 2.89 | 289.90 ± 57.30 | 28.1 ± 5.6 |
| 27 | 1 | 81.36 ± 19.60 | 8.33 ± 2.89 | 1580.28 ± 351.83 | 30.7 ± 6.8 |
| 28 | 1 | 653.86 ± 96.82 | 15.00 ± 8.66 | 15050.59 ± 2720.50 | 36.5 ± 6.6 |

The AUC for Preparations No. 26, No. 13, No. 27 and No. 28 were 49.28 ng·min/mL, 289.90 ng·min/mL, 1580.28 ng·min/mL and 15050.59 ng·min/mL, respectively. The BAs of ghrelin for these preparations were 23.9%, 28.1%, 30.7% and 36.5%, respectively. This observation indicates that the absorption of ghrelin does not reach saturation and keeps increasing as the dose of ghrelin is increased from 10 µg/kg to 2,000 µg/kg.

Example 12

Effects of Benzyl Alcohol on Pharmacokinetics of Subcutaneously Injected Ghrelin in Rats As in Comparative Example 2, Preparations No. 13, No. 14, No. 29 and No. 30 were subcutaneously administered at a dose of 1 mL/kg and the plasma ghrelin levels were measured by RIA method. The pharmacokinetic parameters are shown in Table 17 below.

TABLE 17

Pharmacokinetic parameters of ghrelin preparations
subcutaneously administered to rats (Effects of benzyl alcohol)

| Prepar. No. | Dose volume (mL/kg) | Cmax (ng/mL) | Tmax (min) | AUC (ng · min/mL) | BA (%) |
|---|---|---|---|---|---|
| 13 | 1 | 16.47 ± 2.82 | 6.67 ± 2.89 | 289.90 ± 57.30 | 28.1 ± 5.6 |
| 14 | 1 | 9.08 ± 2.76 | 6.67 ± 2.89 | 142.04 ± 32.17 | 13.8 ± 3.1 |
| 29 | 1 | 19.59 ± 2.58 | 8.33 ± 2.89 | 404.34 ± 80.11 | 39.3 ± 7.8 |
| 30 | 1 | 15.99 ± 3.66 | 5.00 ± 0.00 | 259.89 ± 43.08 | 25.2 ± 4.2 |

The BAs obtained for Preparations No. 13, No. 14, No. 29 and No. 30 were 28.1%, 13.8%, 39.3% and 25.2%, respectively. Thus, the presence of 1% (w/v) benzyl alcohol resulted in a markedly increase in the BA of ghrelin in each of the liquid preparations containing 0.1M or 0.03M sodium acetate buffer serving as an acidic solution, as compared to their benzyl alcohol-free counterparts. This indicates the ability of benzyl alcohol to increase the BA of ghrelin.

Example 13

Effects of the Concentration of Ghrelin on Pharmacokinetics of Subcutaneously Injected Ghrelin in Rats As in Comparative Example 2, Preparations No. 30 and No. 31 were subcutaneously administered. Preparation No. 30 was administered in a volume of 1 mL/kg and Preparation No. 31 in a volume of 50 µL/kg (a microsyringe (SGE. Co., Ltd.) was used to administer 50 µL/kg), so that the same dose 50 µg/kg of ghrelin would be delivered by the two preparations. The blood samples were collected in the same manner as in Comparative Example 2 and the plasma ghrelin levels were measured by RIA method. The pharmacokinetic parameters are shown in Table 18 below.

TABLE 18

Pharmacokinetic parameters of ghrelin preparations subcutaneously
administered to rats (Effects of the concentration of ghrelin)

| Prepar. No. | Dose volume (mL/kg) | Cmax (ng/mL) | Tmax (min) | AUC (ng · min/mL) | BA (%) |
|---|---|---|---|---|---|
| 30 | 1 | 15.99 ± 3.66 | 5.00 ± 0.00 | 259.89 ± 43.08 | 25.2 ± 4.2 |
| 31 | 0.05 | 21.19 ± 1.47 | 6.67 ± 2.89 | 238.83 ± 32.09 | 23.2 ± 3.1 |

The BA of ghrelin in Preparation No. 30 (25.2%) was as high as that in Preparation No. 31 (23.2%). This indicates that the presence of a sodium acetate buffer and benzyl alcohol increases the ghrelin absorption regardless of the concentration and the dose of ghrelin.

Example 14

Effects of the Preparation Process of Acetic Acid Buffer on Pharmacokinetics of Subcutaneously Injected Ghrelin in Rats Preparations No. 31 and No. 32 were subcutaneously administered at a dose of 50 µL/kg, so that the same dose of ghrelin would be delivered by the two preparations (50 µg/kg). The blood samples were collected in the same manner as in Comparative Example 2 and the plasma ghrelin levels were measured by RIA method. The pharmacokinetic parameters are shown in Table 19 below.

TABLE 19

Pharmacokinetic parameters of ghrelin preparations subcutaneously administered to rats (Effects of the preparation process of acetic acid buffer)

| Prepar. No. | Dose volume (mL/kg) | Cmax (ng/mL) | Tmax (min) | AUC (ng · min/mL) | BA (%) |
|---|---|---|---|---|---|
| 31 | 0.05 | 21.19 ± 1.47 | 6.67 ± 2.89 | 238.83 ± 32.09 | 23.2 ± 3.1 |
| 32 | 0.05 | 38.39 ± 28.38 | 5.00 ± 0.00 | 445.28 ± 262.56 | 43.2 ± 25.5 |

The BAs obtained for Preparations No. 31 and No. 32 were 23.2% and 43.2%, respectively. The acidic buffer used in Preparation No. 31 was prepared by adding hydrochloric acid to an aqueous sodium acetate solution to a pH of 4.0, whereas the acidic buffer used in Preparation No. 32 was prepared by adding an aqueous sodium hydroxide solution to acetic acid to a pH of 4.0. The BA of ghrelin was markedly increased in each of the two liquid preparations as compared to the BA obtained for the 5% (w/v) aqueous mannitol solution. This indicates that the presence of an acidic buffer increases the BA of ghrelin regardless of the preparation process of the acidic solution.

Example 15

Effects of Acetic Acid Buffer on Pharmacokinetics of Subcutaneously Injected Ghrelin in Rats As in Comparative Example 2, Preparations No. 32, No. 51, No. 52 and No. 53 were subcutaneously administered at a dose of 1 mL/kg and the plasma ghrelin levels were measured by RIA method. The pharmacokinetic parameters are shown in Table 20 below.

TABLE 20

Pharmacokinetic parameters of ghrelin preparations subcutaneously administered to rats (Effects of the concentration and the pH of acetic acid buffer)

| Prepar. No. | Dose volume (mL/kg) | Cmax (ng/mL) | Tmax (min) | AUC (ng · min/mL) | BA (%) |
|---|---|---|---|---|---|
| 32 | 0.05 | 21.19 ± 1.47 | 6.67 ± 2.89 | 238.83 ± 32.09 | 23.2 ± 3.1 |
| 51 | 1 | 14.52 ± 1.32 | 5.00 ± 0.00 | 234.78 ± 71.01 | 22.8 ± 6.9 |
| 52 | 1 | 11.55 ± 1.62 | 6.67 ± 2.89 | 185.48 ± 24.32 | 18.0 ± 2.4 |
| 53 | 1 | 13.59 ± 3.72 | 5.00 ± 0.00 | 230.71 ± 43.38 | 22.4 ± 4.2 |

The BAs obtained for Preparations No. 32, No. 51, No. 52 and No. 53 were 23.2%, 22.8%, 18.0% and 22.4%, respectively. Preparations No. 32 and No. 51 through No. 53 each contain benzyl alcohol, an alcohol that can increase the BA of ghrelin, and sucrose, along with an acetic acid buffer serving as an acidic solution. Each of these liquid preparations achieved higher BA than was achieved by Preparation No. 79 (14.2%), which contained benzyl alcohol and sucrose, but no acetic acid buffer. This indicates that a liquid ghrelin preparation containing an acidic solution, an alcohol and a sugar can achieve high BA of ghrelin.

Example 16

Effects of Other Acidic Solutions on Pharmacokinetics of Subcutaneously Injected Ghrelin in Rats As in Comparative Example 2, Preparations No. 54 through No. 59 and No. 73 were subcutaneously administered at a dose of 1 mL/kg and the plasma ghrelin levels were measured by RIA method. The pharmacokinetic parameters are shown in Table 21 below.

TABLE 21

Pharmacokinetic parameters of ghrelin preparations subcutaneously administered to rats (Effects of other acidic solutions)

| Prepar. No. | Dose volume (mL/kg) | Cmax (ng/mL) | Tmax (min) | AUC (ng · min/mL) | BA (%) |
|---|---|---|---|---|---|
| 54 | 1 | 13.66 ± 4.85 | 5.00 ± 0.00 | 204.81 ± 48.86 | 19.9 ± 4.7 |
| 55 | 1 | 13.97 ± 5.00 | 5.00 ± 0.00 | 178.41 ± 42.96 | 17.3 ± 4.2 |
| 56 | 1 | 12.16 ± 3.84 | 6.67 ± 2.89 | 229.86 ± 77.72 | 22.3 ± 7.5 |
| 57 | 1 | 11.48 ± 4.49 | 6.67 ± 2.89 | 204.27 ± 87.60 | 19.8 ± 8.5 |
| 58 | 1 | 15.10 ± 0.60 | 5.00 ± 0.00 | 274.07 ± 11.37 | 26.6 ± 1.1 |
| 59 | 1 | 13.52 ± 3.41 | 5.00 ± 0.00 | 238.52 ± 39.24 | 23.2 ± 3.8 |
| 73 | 1 | 8.70 ± 0.96 | 5.00 ± 0.00 | 147.75 ± 25.47 | 14.3 ± 2.5 |

The BAs obtained for Preparations No. 54 through No. 59 and No. 73 were 19.9%, 17.3%, 22.3%, 19.8%, 26.6%, 23.2% and 14.3%, respectively. Preparations No. 54 through 59 each contains benzyl alcohol, an alcohol that can increase the BA of ghrelin, and sucrose, along with an acidic solution. Each of these liquid preparations achieved higher BA than was achieved by Preparation No. 79 (14.2%), which contained benzyl alcohol and sucrose, but no acidic solution. This indicates that a liquid ghrelin preparation containing an acidic buffer, an alcohol and a sugar can achieve high BA of ghrelin. The presence of an acidic solution resulted in an increase in the BA of ghrelin regardless of the make-up of the acidic solution.

Example 17

Effects of Alcohol and Sugar in the Absence of Acidic Solution on Pharmacokinetics of Subcutaneously Injected Ghrelin in Rats As in Comparative Example 2, Preparations No. 78 through No. 80 were subcutaneously administered at a dose of 1 mL/kg and the plasma ghrelin levels were measured by RIA method. The pharmacokinetic parameters are shown in Table 22 below.

TABLE 22

Pharmacokinetic parameters of ghrelin preparations subcutaneously administered to rats (Effects of alcohol and sugar in the absence of acidic solution)

| Prepar. No. | Dose volume (mL/kg) | Cmax (ng/mL) | Tmax (min) | AUC (ng · min/mL) | BA (%) |
|---|---|---|---|---|---|
| 78 | 1 | 4.84 ± 1.60 | 6.67 ± 2.89 | 85.88 ± 11.43 | 8.3 ± 1.1 |
| 79 | 1 | 9.17 ± 3.65 | 5.00 ± 0.00 | 146.27 ± 30.58 | 14.2 ± 3.0 |
| 80 | 1 | 12.11 ± 6.21 | 5.00 ± 0.00 | 174.20 ± 69.76 | 16.9 ± 6.8 |

The BAs obtained for Preparations No. 78 through No. 80 were 8.3%, 14.2% and 16.9%, respectively. The BA of ghrelin in Preparation No. 35 is 3.0%, which contains only sucrose, and it was confirmed that the addition of an alcohol can increase the BA of ghrelin even in the absence of an acidic solution.

Example 18

Effects of Alcohol in the Absence of Acidic Solution on Pharmacokinetics of Subcutaneously Injected Ghrelin in Rats As in Comparative Example 2, Preparations No. 60 through No. 63, No. 71 and No. 72 were subcutaneously administered at a dose of 1 mL/kg and the plasma ghrelin levels were measured by RIA method. The pharmacokinetic parameters are shown in Table 23 below.

TABLE 23

Pharmacokinetic parameters of ghrelin preparations
subcutaneously administered to rats (Effects of alcohol in the absence
of acidic solution)

| Prepar. No. | Dose volume (mL/kg) | Cmax (ng/mL) | Tmax (min) | AUC (ng · min/mL) | BA (%) |
|---|---|---|---|---|---|
| 60 | 1 | 4.96 ± 1.60 | 5.00 ± 0.00 | 78.95 ± 20.93 | 7.7 ± 2.0 |
| 61 | 1 | 7.48 ± 3.20 | 8.33 ± 2.89 | 168.30 ± 82.00 | 16.3 ± 8.0 |
| 62 | 1 | 1.59 ± 0.47 | 13.33 ± 5.77 | 31.39 ± 15.09 | 3.0 ± 1.5 |
| 63 | 1 | 10.95 ± 2.91 | 5.00 ± 0.00 | 202.97 ± 47.31 | 19.7 ± 4.6 |
| 71 | 1 | 10.16 ± 3.54 | 5.00 ± 0.00 | 164.08 ± 51.45 | 15.9 ± 5.0 |
| 72 | 1 | 8.57 ± 2.96 | 5.00 ± 0.00 | 129.60 ± 51.53 | 12.6 ± 5.0 |

The BAs of Preparations No. 60 through No. 63, No. 71 and No. 72 were mostly higher than that of Preparation No. 34 (5.0%), which used physiological saline, and that of Preparation No. 35 (3.0%), which used a 10% (w/v) aqueous sucrose solution. These results indicate that the presence of an alcohol alone can increase the BA of ghrelin even in the absence of an acidic solution.

Example 19

Effects of Non-Alcoholic Polar Organic Liquids in the Absence of Acidic Solutions on Pharmacokinetics of Subcutaneously Injected Ghrelin in Rats As in Comparative Example 2, Preparations No. 64 through No. 68, No. 70, No. 74 and No. 76 were subcutaneously administered at a dose of 1 mL/kg and the plasma ghrelin levels were measured by RIA method. The pharmacokinetic parameters are shown in Table 24 below.

TABLE 24

Pharmacokinetic parameters of ghrelin preparations
subcutaneously administered to rats (Effects of non-alcoholic polar
organic liquids in the absence of acidic solutions)

| Prepar. No. | Dose volume (mL/kg) | Cmax (ng/mL) | Tmax (min) | AUC (ng · min/mL) | BA (%) |
|---|---|---|---|---|---|
| 64 | 1 | 4.12 ± 2.18 | 5.00 ± 0.00 | 75.76 ± 17.40 | 7.4 ± 1.7 |
| 65 | 1 | 9.85 ± 0.57 | 23.33 ± 11.55 | 591.33 ± 66.15 | 57.4 ± 6.4 |
| 66 | 1 | 6.95 ± 1.46 | 30.00 ± 0.00 | 418.55 ± 50.13 | 40.6 ± 4.9 |
| 67 | 1 | 10.47 ± 3.04 | 13.33 ± 5.77 | 655.33 ± 82.39 | 63.6 ± 8.0 |
| 68 | 1 | 9.54 ± 4.00 | 6.67 ± 2.89 | 304.04 ± 144.01 | 29.5 ± 14.0 |
| 70 | 1 | 2.14 ± 1.45 | 15.00 ± 13.23 | 29.59 ± 15.19 | 2.9 ± 1.5 |
| 74 | 1 | 5.07 ± 2.27 | 6.67 ± 2.89 | 89.20 ± 36.34 | 8.7 ± 3.5 |
| 76 | 1 | 3.72 ± 2.21 | 5.00 ± 0.00 | 61.51 ± 33.12 | 6.0 ± 3.2 |

The BAs of Preparations No. 64 through No. 68, No. 70, No. 74 and No. 76 were mostly higher than that of Preparation No. 34 (5.0%), which used physiological saline, and that of Preparation No. 35 (3.0%), which used a 10% (w/v) aqueous sucrose solution. These results indicate that the presence of a polar organic liquid alone can increase the BA of ghrelin even in the absence of an acidic solution. The increase in the BA was most prominent for N-methyl-2-pyrrolidone.

Example 20

Effects of N-methyl-2-pyrrolidone on Pharmacokinetics of Subcutaneously Injected Ghrelin in Rats As in Comparative Example 2, Preparations No. 83 and No. 65 were subcutaneously administered at a dose of 1 mL/kg and the plasma ghrelin levels were measured by RIA method. The pharmacokinetic parameters are shown in Table 25 below.

TABLE 25

Pharmacokinetic parameters of ghrelin preparations
subcutaneously administered to rats (Effects of N-methyl-2-pyrrolidone)

| Prepar. No. | Dose volume (mL/kg) | Cmax (ng/mL) | Tmax (min) | AUC (ng · min/mL) | BA (%) |
|---|---|---|---|---|---|
| 83 | 1 | 16.22 ± 3.13 | 10.00 ± 0.00 | 697.53 ± 102.00 | 67.7 ± 9.9 |
| 65 | 1 | 9.85 ± 0.57 | 23.33 ± 11.55 | 591.33 ± 66.15 | 57.4 ± 6.4 |

Preparations No. 83 and No. 65 both achieved considerably high BAs of 65.7% and 57.4%, respectively. The BA of ghrelin was higher in Preparation No. 83, which contained an acidic solution, than in Preparation No. 65, which did not contain acidic solution. This indicates that the ability of N-methyl-2-pyrrolidone to increase the BA, though high in itself, can be further increased by the addition of an acidic solution.

Example 21

Pharmacokinetics of Intramuscularly Injected Ghrelin in Rats

As with the examples of subcutaneous administration, these rats, inserted a polyethylene tube in the femoral artery, were intramuscularly administered Preparations No. 3 and No. 13 in the femoral muscle at a dose of 1 mL/kg, using a syringe and a 26 G needle. The blood samples were collected in the same manner as in Comparative Example 2 and the plasma ghrelin levels were measured by RIA method. The results are shown in FIG. 6. The pharmacokinetic parameters are shown in Table 26 below.

TABLE 26

Pharmacokinetic parameters of ghrelin preparations
intramuscularly administered to rats (Effects of sodium acetate buffer)

| Prepar. No. | Dose volume (mL/kg) | Cmax (ng/mL) | Tmax (min) | AUC (ng · min/mL) | BA (%) |
|---|---|---|---|---|---|
| 3 | 1 | 9.93 ± 3.64 | 5.00 ± 0.00 | 111.92 ± 39.98 | 10.9 ± 3.9 |
| 13 | 1 | 16.82 ± 3.39 | 8.33 ± 2.89 | 293.78 ± 89.38 | 28.5 ± 8.7 |

The BAs obtained for Preparations No. 3 and No. 13 intramuscularly administered were 10.9% and 28.5% with respect to the case where they were intravenously administered, respectively. Thus, the BA of ghrelin in the presence of the sodium acetate buffer was 2.6 times higher than the BA of ghrelin obtained for the 5% (w/v) aqueous mannitol solution. This indicates that sodium acetate buffers can increase the absorption of ghrelin in intramuscular administration as effectively as they can in subcutaneous administration.

Example 22

Pharmacokinetics of Ghrelin in Cynomolgus Monkeys

Preparations No. 5 and No. 33 were subcutaneously administered to separate groups of cynomolgus monkeys and the plasma ghrelin levels were measured. Furthermore, Preparation No. 1 was intravenously administered to another group of cynomolgus monkeys. The plasma ghrelin levels were measured.

Each group consisted of three male monkeys (imported from China) aged 4 to 6 years. Preparations No. 5 and No. 33 were subcutaneously injected in the dorsal skin at a dose of 0.2 mL/body using a syringe and a 26 G needle (each available from Terumo Co., Ltd.).

Using a syringe and a 26 G needle (each available from Terumo Co., Ltd.), Preparation No. 1 was intravenously injected in the forearm vena cephalica at a dose of 2 mL/kg.

In each case, blood samples were collected from the forearm vena cephalica before administration and 5, 10, 15, 30, 40, 60, 90, and 120 minutes after administration. To each sample, one-hundredth as much of an EDTA.2Na.2H$_2$O solution and one-fiftieth as much of an AEBSF solution were added immediately after collection of the sample. The sample was then centrifuged to separate plasma, to which one-tenth as much 1N hydrochloric acid was immediately added. The sample was mixed and stored at −80° C. until analysis.

The plasma samples were then analyzed for the ghrelin levels by Enzyme-Linked Immunosolvent Assay (ELISA) using Active Ghrelin ELISA Kit (Cat. No. MM-401, Mitsubishi Kagaku Iatron Inc.). Similarly to RIA, this assay can specifically detect the active ghrelin.

FIG. 7 shows the changes in the plasma ghrelin concentrations over time. The results shown in FIG. 7 were used to determine $C_{max}$ and $T_{max}$ for each liquid preparation. Using the trapezoidal method, the AUC was also calculated for each preparation. The AUCs were then used to determine the BA of ghrelin. The results are shown in Table 27. These values were obtained as averages of the data obtained for the three cynomolgus monkeys in each group.

TABLE 27

Pharmacokinetic parameters of ghrelin preparations intravenously or subcutaneously administered to cynomolgus monkeys

| Prepar. No. Route of administ. | Dose volume | Dosage (μg/kg) | $C_0$ or Cmax (ng/mL) | Tmax (min) | AUC (ng · min/mL) | BA (%) |
|---|---|---|---|---|---|---|
| 1 i.v. | 2 mL/kg | 10 | 126.53 ± 27.67 | — | 1290.83 ± 165.21 | — |
| 5 s.c. | 0.2 mL/body | 108 ± 3 | 39.66 ± 8.22 | 6.67 ± 2.89 | 684.33 ± 47.00 | 4.9 ± 0.5 |
| 33 s.c. | 0.2 mL/body | 100 ± 14 | 66.31 ± 9.68 | 6.67 ± 2.89 | 1586.10 ± 646.73 | 12.8 ± 5.8 |

The BAs obtained for the subcutaneous Preparations No. 5 and No. 33 were 4.9% and 12.8% with respect to the case where they were intravenously administered, respectively. Thus, the BA of ghrelin was 2.6 times higher in the liquid preparation formulated with a sodium acetate buffer and 1% (w/v) benzyl alcohol than in the liquid preparation formulated with a 5% (w/v) aqueous mannitol solution. This indicates that sodium acetate buffer containing benzyl alcohol can increase the absorption of ghrelin in cynomolgus monkeys as effectively as it can in rats.

Example 23

The Ability of Ghrelin Preparation to Increase the Plasma Growth Hormone Levels in Rats Preparations No. 4 and No 31 were used to examine the ability of ghrelin preparations to increase the plasma concentration of growth hormone (GH) in rats.

7-week old, male SD rats (Charles River Laboratories Japan Inc.) were used. Each preparation was administered to a group of these rats inserted a polyethylene tube (PE-50, Clay Adams Co., Ltd.) in the femoral artery.

Using a syringe and a 26 G needle (available from Terumo Co., Ltd.), each preparation was subcutaneously administered in the dorsal skin at a dose of 50 μL/kg. Blood samples were collected from the polyethylene tube in the femoral artery before administration and 5, 10, 20, 30 and 60 minutes after administration.

To each sample, one-hundredth as much of an EDTA.2Na.2H₂O solution was added immediately after collection of the sample. The samples were then centrifuged to separate plasma, which in turn was stored at −80° C. until analysis.

The plasma samples were analyzed for the GH concentrations by radioimmunoassay (RIA) using Rat Growth Hormone (rGH) [$^{125}$I] assay system (Amersham Bioscience Co., Ltd.: Cat. No. RPA551). FIG. 8 shows the changes in the plasma GH concentrations over time. These values were obtained as averages of the data obtained for the three rats in each group.

As can be seen from the results shown in FIG. 8, the plasma GH concentration increased slightly from the initial value (113 ng/mL) and reached its peak value (208 ng/mL) 5 minutes after the subcutaneous administration of Preparation No. 4. In comparison, the plasma GH concentration peaked (316 ng/mL) 20 minutes after the subcutaneous administration of Preparation No. 31. The peak value was 3.3 times higher than the initial value (96 ng/mL). These results indicate that the increase in the plasma GH concentration is more prominent for the preparation using sodium acetate and benzyl alcohol.

Example 24

Pharmacokinetics of Other Types of Ghrelin Subcutaneously Injected in Rats

As in Comparative Example 2, Preparations No. 37, No. 39, No 41, and No. 98 through No. 102 were subcutaneously administered at a dose of 1 mL/kg and the plasma ghrelin levels were measured by RIA. The pharmacokinetic parameters are shown in Table 28 below. As in Comparative Example 2, Preparations No. 36, No. 38 and No. 40 were intravenously administered at a dose of 1 mL/kg and the plasma ghrelin levels were measured by RIA. The plasma concentrations were used to determine the BA for each type of ghrelin.

The plasma levels of rat ghrelin were measured in the same manner as with human ghrelin. The plasma levels of human ghrelin and des-octanoyl ghrelin were measured by radioimmunoassay (RIA) using an anti-ghrelin antibody. Specifically, the anti-ghrelin antibody and then [$^{125}$I-Tyr]ghrelin(13-28) were added to each plasma sample for competition. Subsequently, a secondary antibody was added to precipitate the antibody-ghrelin complex. The supernatant was separated and analyzed for radioactivity by a γ-counter (Packard Instruments Co., Ltd.). The anti-ghrelin antibody used in the assay can recognize des-octanoyl ghrelin as well as ghrelin.

The plasma levels of aminododecan human ghrelin (Adod ghrelin) were measured by radioimmunoassay (RIA) using an anti-Adod ghrelin antibody. Specifically, the anti-Adod ghrelin antibody and then $^{125}$I-labelled antigen were added to each plasma sample for competition. Subsequently, a secondary antibody was added to precipitate the antibody-Adod ghrelin complex. The supernatant was separated and analyzed for radioactivity by a γ-counter (Packard Instruments Co., Ltd.).

TABLE 28

Pharmacokinetic parameters of different types of ghrelin subcutaneously injected in rats

| Prepar. No. Route of administ. | Dose volume (mL/kg) | Cmax (ng/mL) | Tmax (min) | AUC (ng · min/mL) | BA (%) |
|---|---|---|---|---|---|
| 36 i.v. | 1 | 188.34 ± 180.25 | — | 478 ± 198 | — |
| 37 s.c. | 1 | 3.94 ± 1.71 | 5.00 ± 0.00 | 55.58 ± 12.99 | 4.7 ± 1.1 |

TABLE 28-continued

Pharmacokinetic parameters of different types of ghrelin subcutaneously injected in rats

| Prepar. No. Route of administ. | Dose volume (mL/kg) | Cmax (ng/mL) | Tmax (min) | AUC (ng · min/mL) | BA (%) |
|---|---|---|---|---|---|
| 98 s.c. | 1 | 20.34 ± 2.99 | 6.67 ± 2.89 | 332.40 ± 64.97 | 27.8 ± 5.4 |
| 38 i.v. | 1 | 45.15 ± 4.04 | — | 584.69 ± 71.77 | — |
| 39 s.c. | 1 | 24.79 ± 5.56 | 16.67 ± 5.77 | 636.02 ± 139.77 | 21.7 ± 4.8 |
| 99 s.c. | 1 | 44.35 ± 5.56 | 16.67 ± 5.77 | 1047.20 ± 185.63 | 35.8 ± 6.3 |
| 100 s.c. | 1 | 47.12 ± 4.39 | 16.67 ± 5.77 | 1212.94 ± 91.19 | 41.5 ± 3.1 |
| 101 s.c. | 1 | 52.67 ± 8.45 | 16.67 ± 5.77 | 1252.98 ± 115.29 | 42.8 ± 3.9 |
| 40 i.v. | 1 | 154.65 ± 10.13 | — | 2991.13 ± 173.15 | — |
| 41 s.c. | 1 | 6.67 ± 3.30 | 20.00 ± 10.00 | 291.67 ± 124.33 | 3.9 ± 1.7 |
| 102 s.c. | 1 | 52.27 ± 5.43 | 10.00 ± 0.00 | 2194.50 ± 341.83 | 29.3 ± 4.6 |

The results demonstrate that liquid preparations containing a polar organic liquid, an acidic solution, a sugar and an alcohol can markedly increase not only the BA of subcutaneously injected human ghrelin, but also the BAs of subcutaneously injected other ghrelins, including rat ghrelin, des-octanoyl ghrelin (human ghrelin that does not have the octanoyl modification on Ser3) and human [L-2-aminododecanoic acid$^3$]ghrelin.

Example 25

Pharmacokinetics of Other Physiologically Active Peptides and Proteins Subcutaneously Injected in Rats As in Comparative Example 2, Preparations No. 43, 45, 47, 49, 50, and 103 through 107 were subcutaneously administered at a dose of 1 mL/kg and the plasma levels of the peptides and proteins were measured by RIA. The pharmacokinetic parameters are shown in Table 29 below. As in Comparative Example 2, Preparations No. 42, 44, 46 and 48 were intravenously administered at a dose of 1 mL/kg and the plasma levels of the peptides and proteins were measured by RIA. The plasma concentrations were used to determine the BA for each peptide or protein.

The plasma levels of human parathyroid hormone (1-34) (hPTH) were measured by radioimmunoassay (RIA) using an anti-PTH antibody. Specifically, the anti-PTH antibody and then [$^{125}$I-Tyr34]PTH(1-34) were added to each plasma sample for competition. Subsequently, a secondary antibody was added to precipitate the antibody-PTH(1-34) complex. The supernatant was separated and analyzed for radioactivity by a γ-counter (Packard Instruments Co., Ltd.).

The plasma levels of human glucagon-like peptide-1 (GLP-1) were measured by Enzyme-Linked Immunosolvent Assay (ELISA) using Glucagon-like Peptide-1 (Active) ELISA Kit (LINCO Research Inc.).

The plasma levels of human adrenomedullin were measured by radioimmunoassay (RIA) using AM mature RIA Shionogi (Shionogi Co., Ltd).

The plasma levels of human insulin were measured by radioimmunoassay (RIA) using Insulin-RIA-bead II (Yamasa Co., Ltd.).

The plasma levels of human atrial natriuretic peptide (hANP) were measured by radioimmunoassay (RIA) using Shiono RIA ANP (Shionogi Co., Ltd.).

TABLE 29

Pharmacokinetic parameters of other physiologically active peptides and proteins subcutaneously administered to rats

| Prepar. No. Route of administ. | Dose volume (mL/kg) | Cmax (ng/mL) | Tmax (min) | AUC (ng · min/mL) | BA (%) |
|---|---|---|---|---|---|
| 42 i.v. | 1 | 413 ± 291 | — | 294 ± 184 | — |
| 43 s.c. | 1 | 1.74 ± 0.86 | 5.00 ± 0.00 | 24.00 ± 7.26 | 4.9 ± 1.5 |
| 103 s.c. | 1 | 5.74 ± 0.47 | 5.00 ± 0.00 | 68.50 ± 6.95 | 14.0 ± 1.4 |
| 44 i.v. | 1 | 995 ± 178 | — | 1136 ± 142 | — |
| 45 s.c. | 1 | 5.46 ± 3.55 | 5.00 ± 0.00 | 71.64 ± 51.00 | 6.3 ± 4.5 |
| 104 s.c. | 1 | 11.89 ± 1.95 | 5.00 ± 0.00 | 162.37 ± 19.63 | 14.3 ± 1.7 |

TABLE 29-continued

Pharmacokinetic parameters of other physiologically active peptides and proteins subcutaneously administered to rats

| Prepar. No. Route of administ. | Dose volume (mL/kg) | Cmax (ng/mL) | Tmax (min) | AUC (ng · min/mL) | BA (%) |
|---|---|---|---|---|---|
| 46 i.v. | 1 | 30.90 ± 19.33 | — | 201.8 ± 4.0 | — |
| 47 s.c. | 1 | 0.89 ± 0.92 | 16.67 ± 5.77 | 30.10 ± 30.93 | 7.5 ± 7.7 |
| 105 s.c. | 1 | 1.81 ± 0.38 | 6.67 ± 2.89 | 42.29 ± 12.98 | 10.5 ± 3.2 |
| 48 i.v. | 1 | 216.36 ± 19.31 | — | 2423.3 ± 288.7 | — |
| 49 s.c. | 1 | 11.66 ± 8.98 | 11.67 ± 5.7 | 320.77 ± 133.23 | 13.2 ± 5.5 |
| 106 s.c. | 1 | 16.34 ± 1.77 | 15.00 ± 0.00 | 626.68 ± 48.25 | 25.9 ± 2.0 |
| 50 s.c. | 1 | 8.17 ± 1.74 | 20.00 ± 8.66 | 388.04 ± 113.97 | 18.5 ± 5.4 |
| 107 s.c. | 1 | 27.30 ± 3.95 | 15.00 ± 0.00 | 1254.64 ± 397.47 | 59.8 ± 18.9 |

The results demonstrate that liquid peptide preparations containing a sugar, an alcohol and an acidic solution can markedly increase not only the BA of subcutaneously injected human ghrelin, but also the BAs of subcutaneously injected other peptides, including rat ghrelin, des-octanoyl ghrelin (human ghrelin that does not have the octanoyl modification on Ser3), [L-2-aminododecanoic acid$^3$] human ghrelin, human glucagon-like peptide-1 (GLP-1), human atrial natriuretic peptide (hANP), human adrenomedullin, human parathyroid hormone (hPTH(1-34)) and human insulin.

Production Example 1

Preparation of pH-Adjusted Pharmaceutical Composition Containing Human Ghrelin

Human ghrelin which is one of ghrelins, was dissolved in purified water to form an aqueous solution containing about 0.15 μmol/mL (=0.5 mg/mL) human ghrelin. While the pH of this solution was monitored, 0.1M aqueous hydrochloric acid was added in small amounts to a final pH of 4.0. This gave a pharmaceutical composition as an aqueous solution containing human ghrelin.

Production Example 2

Preparation of Pharmaceutical Composition Consisting of Rat Ghrelin Dissolved in Acetic Acid Buffer Rat ghrelin which is one of ghrelins, was dissolved in 0.05M acetic acid buffer (pH 4.0) to form a pharmaceutical composition as an aqueous solution containing about 0.15 μmol/mL (=0.5 mg/mL) rat ghrelin. The aqueous solution was determined to have a pH of 4.0.

Production Example 3

Preparation of Pharmaceutical Composition Containing Human Ghrelin

Human ghrelin which is one of ghrelins, and benzyl alcohol were added to 0.05M acetic acid buffer (pH 4.0) to form a pharmaceutical composition as an aqueous solution containing about 0.15 μmol/mL (=0.5 mg/mL) human ghrelin and about 1% (w/v) benzyl alcohol. The aqueous solution was determined to have a pH of 4.0.

Production Example 4

Preparation of Pharmaceutical Composition Containing Human Ghrelin

Human ghrelin which is one of ghrelins, benzyl alcohol and sucrose were added to purified water to form a pharmaceutical composition as an aqueous solution containing about 0.15 μmol/mL (=0.5 mg/mL) human ghrelin, about 1% (w/v) benzyl alcohol and 10% (w/v) sucrose. The aqueous solution was determined to have a pH of 4.7.

Production Example 5

Preparation of Pharmaceutical Composition Containing Human Ghrelin

Human ghrelin, which is one of ghrelins, benzyl alcohol and sucrose were added to 0.1M acetic acid buffer (pH 4.0) to form a pharmaceutical composition as an aqueous solution containing about 0.15 μmol/mL (=0.5 mg/mL) human ghrelin, about 1% (w/v) benzyl alcohol and 10% (w/v) sucrose. The aqueous solution was determined to have a pH of 4.0.

INDUSTRIAL APPLICABILITY

As set forth, the present invention provides an effective liquid preparation that achieves high bioavailability (BA) of physiologically active peptides or proteins, including ghrelin, that are administered as drugs. The present invention also provides a method for improving the bioavailability of physiologically active peptides or proteins, including ghrelin, that are subcutaneously injected in aqueous solutions.

In general, subcutaneously administered physiologically active peptides and proteins are digested by proteases etc, so that their BA becomes lower than is achieved by intravenous injection. The liquid preparation of the present invention containing a physiologically active peptide or protein, such as ghrelins, can be subcutaneously injected to maintain effective blood levels of the peptide or protein. Thus, the present invention is of significant medical importance.

Figure 1:
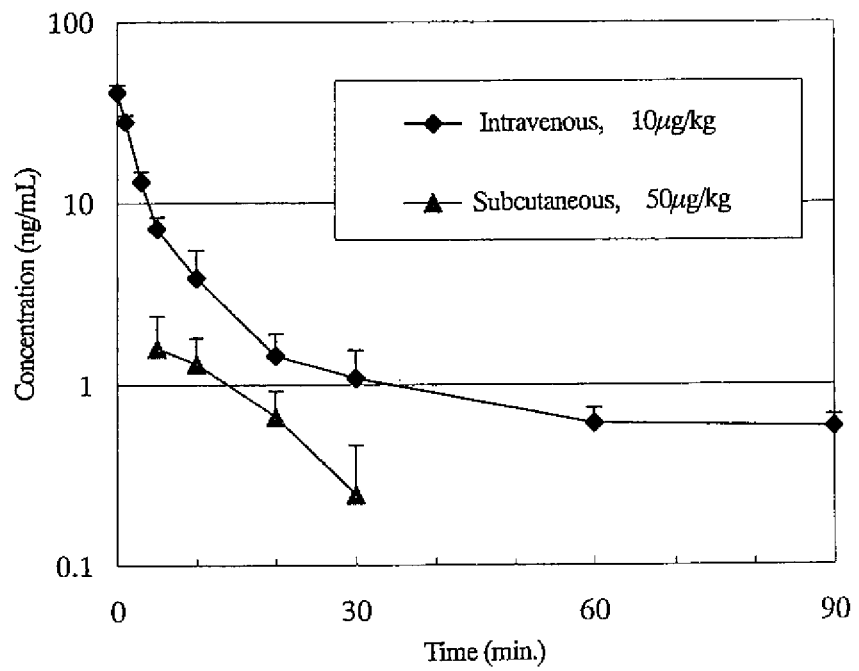
FIG. 1 is a graph showing the changes over time in the plasma levels of human ghrelin intravenously or subcutaneously administered to rats, the human ghrelin being dissolved in a 5% (w/v) aqueous mannitol solution (Comparative Example 2).
Figure 2:
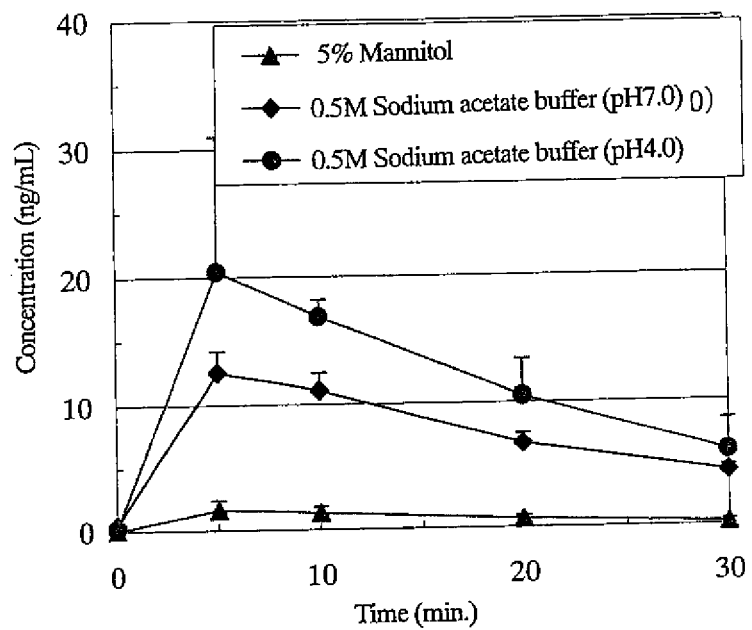
FIG. 2 is a graph showing the changes over time in the plasma levels of human ghrelin subcutaneously administered to rats, the human ghrelin being dissolved in a sodium acetate buffer (Example 2).
Figure 3:
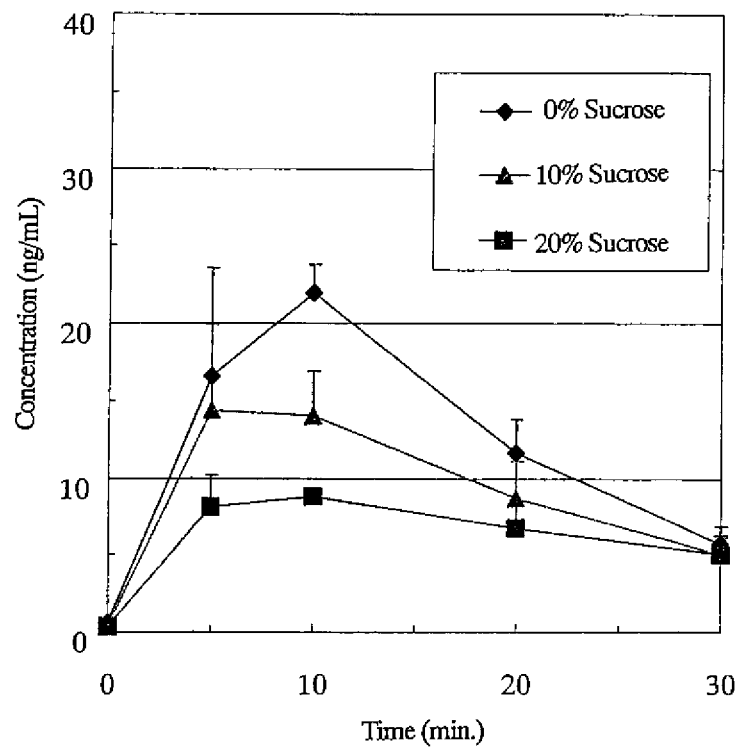
FIG. 3 is a graph showing the changes over time in the plasma levels of human ghrelin subcutaneously administered to rats, the human ghrelin being dissolved in a 0.1M sodium acetate buffer (pH 4.0) containing 0 to 20% (w/v) sucrose (Example 7).
Figure 4:
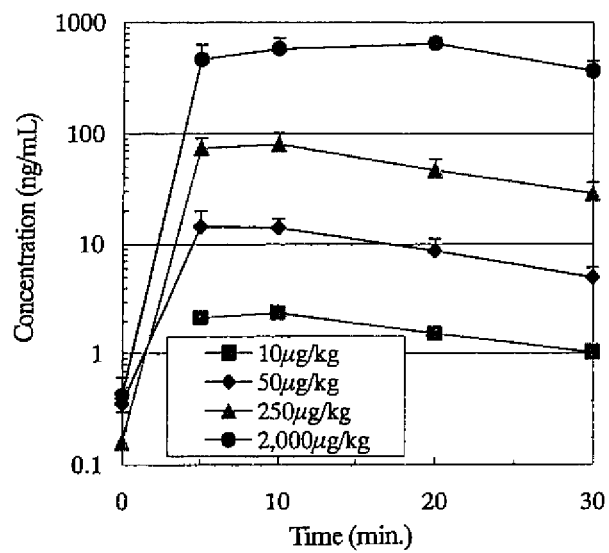
FIG. 4 is a graph showing the changes over time in the plasma levels of ghrelin subcutaneously administered to rats at a dose of 10, 50, 250 or 2,000 μg/kg (Example 8). The preparation contains 0.1M sodium acetate buffer (pH 4.0) and 10% (w/v) sucrose.
Figure 5:
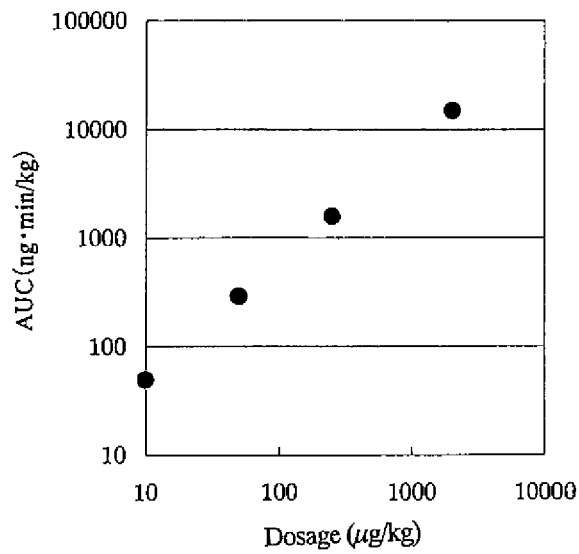
FIG. 5 is a graph showing the relationship between the dose of ghrelin administered to rats at a dose of 10, 50, 250 or 2,000 μg/kg, and the AUCs (Example 8).
Figure 6:
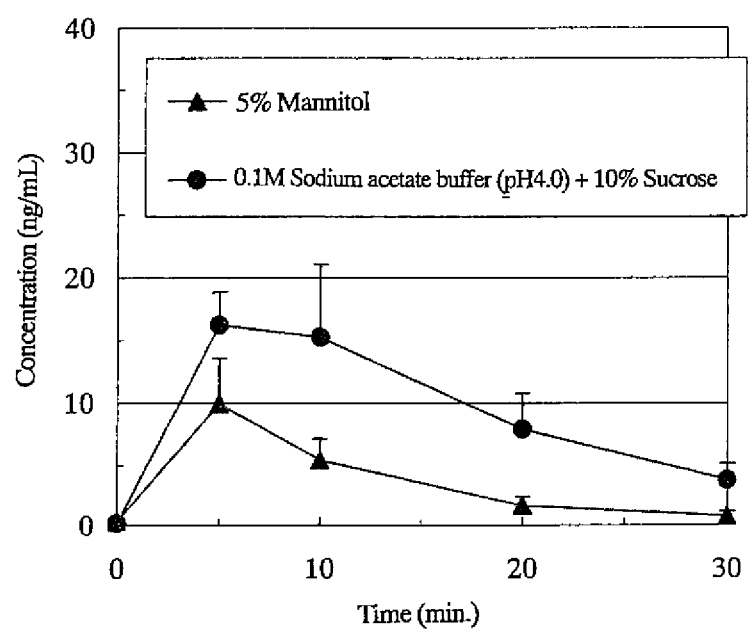
FIG. 6 is a graph showing the changes over time in the plasma levels of human ghrelin intramuscularly administered to rats, the human ghrelin being dissolved in a 5% (w/v) aqueous mannitol solution or in a sodium acetate buffer (Example 12).
Figure 7:
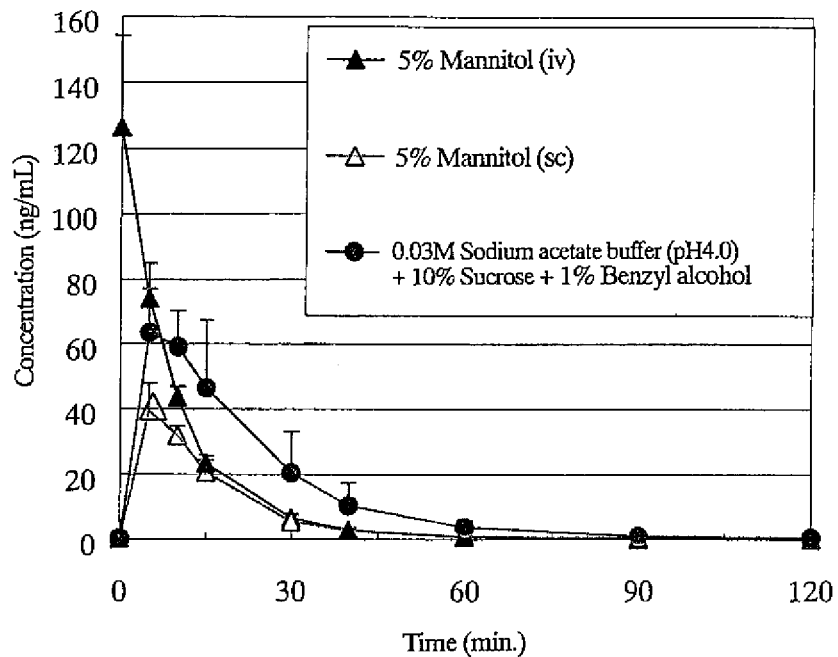
FIG. 7 is a graph showing the changes over time in the plasma levels of human ghrelin intravenously or subcutaneously administered to cynomolgus monkeys, the human ghrelin being dissolved in a 5% (w/v) aqueous mannitol solution or in a sodium acetate buffer (Example 13).
Figure 8:
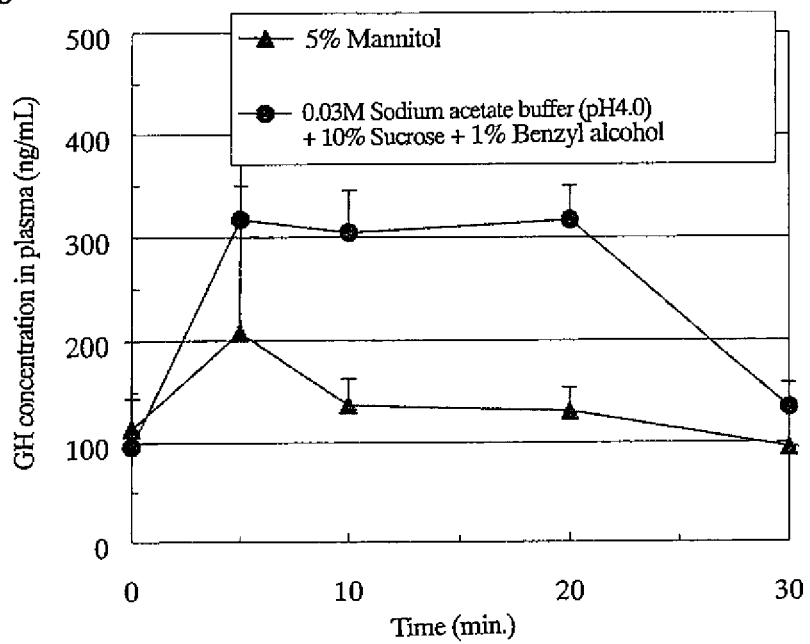
FIG. 8 is a graph showing the changes over time in the plasma levels of growth hormone in rats following the subcutaneous administration of human ghrelin dissolved in a 5% (w/v) aqueous mannitol solution or in a sodium acetate buffer (Example 14).

The invention claimed is:

1. A method for improving bioavailability of one or more ghrelins, comprising,
   (a) adding an acidic solution and a polar organic liquid to an aqueous solution of said one or more ghrelins, or
   (b) adding a polar organic liquid alone to an aqueous solution of said one or more ghrelins,
   wherein the one or more ghrelins is human ghrelin, rat ghrelin, human des-octanoyl ghrelin, human [L-2-aminododecanoic acid$^3$]ghrelin or combinations thereof;
   wherein the acidic solution is acetic acid, lactic acid, phosphoric acid, propionic acid, butyric acid, salts thereof, or combinations thereof; and
   wherein the polar organic liquid is benzyl alcohol, phenol, tert-butanol, N-methyl-2-pyrrolidone, dimethylformamide, dimethylsulfoxide, or combinations thereof.

2. The method according to claim 1, wherein the concentration of the polar organic liquid is from 0.1 to 10% (w/v).

3. The method according to claim 1, further comprising adding a sugar of mannitol, sucrose, glucose, cyclodextrin, or combinations thereof.

4. The method according to claim 3, wherein the sugar is cyclodextrin.

5. The method according to claim 3, wherein the concentration of the sugar is from 1 to 10% (w/v).

6. The method according to claim 1, wherein the ghrelin is human ghrelin.

7. The method according to claim 1, wherein the concentration of the one or more ghrelins is from 50 to 2000 μg/mL.

8. A method for preparing a liquid preparation in order to improve a bioavailability of one or more ghrelins, comprising,
   (a) adding an acidic solution and a polar organic liquid to an aqueous solution of said one or more ghrelins, or
   (b) adding a polar organic liquid alone to an aqueous solution of said one or more ghrelins,
   wherein the ghrelins is human ghrelin, rat ghrelin, human des-octanoyl ghrelin, human [L-2-aminododecanoic acid$^3$]ghrelin, or combinations thereof;
   wherein the acidic solution is acetic acid, lactic acid, phosphoric acid, propionic acid, butyric acid, salts thereof, or combinations thereof; and
   wherein the polar organic liquid is benzyl alcohol, phenol, tert-butanol, N-methyl-2-pyrrolidone, dimethylformamide, dimethylsulfoxide, or combinations thereof.

9. The method of claim 8, wherein the ghrelin is human ghrelin.

10. A method for improving bioavailability of one or more ghrelins, comprising,
   (a) adding an acidic solution and a polar organic liquid to an aqueous solution of said one or more ghrelins, or
   (b) adding a polar organic liquid alone to an aqueous solution of said one or more ghrelins,
   wherein the polar organic liquid is benzyl alcohol, phenol, tert-butanol, N-methyl-2-pyrrolidone, dimethylformamide, dimethylsulfoxide, or combinations thereof.

* * * * *

```
                              SEQUENCE LISTING

<160> NUMBER OF SEQ ID NOS: 21

<210> SEQ ID NO 1
<211> LENGTH: 28
<212> TYPE: PRT
<213> ORGANISM: Homo sapiens
<220> FEATURE:
<221> NAME/KEY: Peptide
<222> LOCATION: (1)..(28)
<223> OTHER INFORMATION: Amino acid sequence for human endogenous
      peptides of growth hormone secretagogue

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
<220> FEATURE:
<221> NAME/KEY: Peptide
<222> LOCATION: (1)..(27)
<223> OTHER INFORMATION: Amino acid sequence for human endogenous
      peptides (27 amino acids) of growth hormone secretagogue

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Rattus norvegicus
<220> FEATURE:
<221> NAME/KEY: Peptide
<222> LOCATION: (1)..(28)
<223> OTHER INFORMATION: Amino acid sequence for rat endogenous peptides
      of growth hormone secretagogue

<400> SEQUENCE: 3
```

-continued

```
Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Rattus norvegicus
<220> FEATURE:
<221> NAME/KEY: Peptide
<222> LOCATION: (1)..(27)
<223> OTHER INFORMATION: Amino acid sequence for rat endogenous peptides
      of growth hormone secretagogue

<400> SEQUENCE: 4

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 5
<211> LENGTH: 28
<212> TYPE: PRT
<213> ORGANISM: Mus musculus
<220> FEATURE:
<221> NAME/KEY: Peptide
<222> LOCATION: (1)..(28)
<223> OTHER INFORMATION: Amino acid sequence for mouse endogenous
      peptides of growth hormone secretagogue

<400> SEQUENCE: 5

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa
<220> FEATURE:
<221> NAME/KEY: Peptide
<222> LOCATION: (1)..(28)
<223> OTHER INFORMATION: Amino acid sequence for porcine endogenous
      peptides of growth hormone secretagogue

<400> SEQUENCE: 6

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Bos taurus
<220> FEATURE:
<221> NAME/KEY: Peptide
<222> LOCATION: (1)..(27)
<223> OTHER INFORMATION: Amino acid sequence for bovine endogenous
      peptides (27 amino acids) of growth hormone secretagogue

<400> SEQUENCE: 7

Gly Ser Ser Phe Leu Ser Pro Glu His Gln Lys Leu Gln Arg Lys Glu
1               5                   10                  15
```

```
Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries
<220> FEATURE:
<221> NAME/KEY: Peptide
<222> LOCATION: (1)..(27)
<223> OTHER INFORMATION: Amino acid sequence for ovine endogenous
      peptides (27 amino acids) of growth hormone secretagogue

<400> SEQUENCE: 8

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 9
<211> LENGTH: 28
<212> TYPE: PRT
<213> ORGANISM: Canis familiaris
<220> FEATURE:
<221> NAME/KEY: Peptide
<222> LOCATION: (1)..(28)
<223> OTHER INFORMATION: Amino acid sequence for dog endogenous peptides
      of growth hormone secretagogue

<400> SEQUENCE: 9

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 21
<212> TYPE: PRT
<213> ORGANISM: Anguilla japonica
<220> FEATURE:
<221> NAME/KEY: Peptide
<222> LOCATION: (1)..(21)
<223> OTHER INFORMATION: Amino acid sequence for eel endogenous peptides
      of growth hormone secretagogue. This peptide is amidated at
      C-terminus.

<400> SEQUENCE: 10

Gly Ser Ser Phe Leu Ser Pro Ser Gln Arg Pro Gln Gly Lys Asp Lys
1               5                   10                  15

Lys Pro Pro Arg Val
            20

<210> SEQ ID NO 11
<211> LENGTH: 23
<212> TYPE: PRT
<213> ORGANISM: Oncorhynchus mykiss
<220> FEATURE:
<221> NAME/KEY: Peptide
<222> LOCATION: (1)..(23)
<223> OTHER INFORMATION: Amino acid sequence for rainbow trout
      endogenous peptides (23 amino acids) of growth hormone
      secretagogue. This peptide is amidated at C-terminus.

<400> SEQUENCE: 11

Gly Ser Ser Phe Leu Ser Pro Ser Gln Lys Pro Gln Val Arg Gln Gly
1               5                   10                  15
```

Lys Gly Lys Pro Pro Arg Val
            20

<210> SEQ ID NO 12
<211> LENGTH: 20
<212> TYPE: PRT
<213> ORGANISM: Oncorhynchus mykiss
<220> FEATURE:
<221> NAME/KEY: Peptide
<222> LOCATION: (1)..(20)
<223> OTHER INFORMATION: Amino acid sequence for rainbow trout
      endogenous peptides (20 amino acids) of growth hormone
      secretagogue. This peptide is amidated at C-terminus.

<400> SEQUENCE: 12

Gly Ser Ser Phe Leu Ser Pro Ser Gln Lys Pro Gln Gly Lys Gly Lys
1               5                   10                  15

Pro Pro Arg Val
            20

<210> SEQ ID NO 13
<211> LENGTH: 24
<212> TYPE: PRT
<213> ORGANISM: Gallus domesticus
<220> FEATURE:
<221> NAME/KEY: Peptide
<222> LOCATION: (1)..(24)
<223> OTHER INFORMATION: Amino acid sequence for chicken endogenous
      peptides of growth hormone secretagogue

<400> SEQUENCE: 13

Gly Ser Ser Phe Leu Ser Pro Thr Tyr Lys Asn Ile Gln Gln Gln Lys
1               5                   10                  15

Gly Thr Arg Lys Pro Thr Ala Arg
            20

<210> SEQ ID NO 14
<211> LENGTH: 24
<212> TYPE: PRT
<213> ORGANISM: Gallus domesticus
<220> FEATURE:
<221> NAME/KEY: Peptide
<222> LOCATION: (1)..(24)
<223> OTHER INFORMATION: Amino acid sequence for chicken endogenous
      peptides of growth hormone secretagogue

<400> SEQUENCE: 14

Gly Ser Ser Phe Leu Ser Pro Thr Tyr Lys Asn Ile Gln Gln Gln Lys
1               5                   10                  15

Asp Thr Arg Lys Pro Thr Ala Arg
            20

<210> SEQ ID NO 15
<211> LENGTH: 26
<212> TYPE: PRT
<213> ORGANISM: Gallus domesticus
<220> FEATURE:
<221> NAME/KEY: Peptide
<222> LOCATION: (1)..(26)
<223> OTHER INFORMATION: Amino acid sequence for chicken endogenous
      peptides of growth hormone secretagogue

<400> SEQUENCE: 15

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
            20                  25

```
<210> SEQ ID NO 16
<211> LENGTH: 27
<212> TYPE: PRT
<213> ORGANISM: Rana catesbeiana
<220> FEATURE:
<221> NAME/KEY: Peptide
<222> LOCATION: (1)..(27)
<223> OTHER INFORMATION: Amino acid sequence for frog endogenous
      peptides of growth hormone secretagogue

<400> SEQUENCE: 16

Gly Leu Thr Phe Leu Ser Pro Ala Asp Met Gln Lys Ile Ala Glu Arg
1               5                   10                  15

Gln Ser Gln Asn Lys Leu Arg His Gly Asn Met
            20                  25

<210> SEQ ID NO 17
<211> LENGTH: 28
<212> TYPE: PRT
<213> ORGANISM: Rana catesbeiana
<220> FEATURE:
<221> NAME/KEY: Peptide
<222> LOCATION: (1)..(28)
<223> OTHER INFORMATION: Amino acid sequence for frog endogenous
      peptides of growth hormone secretagogue

<400> SEQUENCE: 17

Gly Leu Thr Phe Leu Ser Pro Ala Asp Met Gln Lys Ile Ala Glu Arg
1               5                   10                  15

Gln Ser Gln Asn Lys Leu Arg His Gly Asn Met Asn
            20                  25

<210> SEQ ID NO 18
<211> LENGTH: 20
<212> TYPE: PRT
<213> ORGANISM: Tilapia nilotica
<220> FEATURE:
<221> NAME/KEY: Peptide
<222> LOCATION: (1)..(20)
<223> OTHER INFORMATION: Amino acid sequence for tilapia endogenous
      peptides of growth hormone secretagogue. Amidation

<400> SEQUENCE: 18

Gly Ser Ser Phe Leu Ser Pro Ser Gln Lys Pro Gln Asn Lys Val Lys
1               5                   10                  15

Ser Ser Arg Ile
            20

<210> SEQ ID NO 19
<211> LENGTH: 22
<212> TYPE: PRT
<213> ORGANISM: Silurus asotus
<220> FEATURE:
<221> NAME/KEY: Peptide
<222> LOCATION: (1)..(22)
<223> OTHER INFORMATION: Amino acid sequence for catfish endogenous
      peptides of growth hormone secretagogue. This peptide is amidated
      at C-terminus.

<400> SEQUENCE: 19

Gly Ser Ser Phe Leu Ser Pro Thr Gln Lys Pro Gln Asn Arg Gly Asp
1               5                   10                  15

Arg Lys Pro Pro Arg Val
            20
```

```
<210> SEQ ID NO 20
<211> LENGTH: 23
<212> TYPE: PRT
<213> ORGANISM: Silurus asotus
<220> FEATURE:
<221> NAME/KEY: Peptide
<222> LOCATION: (1)..(23)
<223> OTHER INFORMATION: Amino acid sequence for catfish endogenous
      peptides of growth hormone secretagogue

<400> SEQUENCE: 20

Gly Ser Ser Phe Leu Ser Pro Thr Gln Lys Pro Gln Asn Arg Gly Asp
1               5                   10                  15

Arg Lys Pro Pro Arg Val Gly
            20

<210> SEQ ID NO 21
<211> LENGTH: 28
<212> TYPE: PRT
<213> ORGANISM: Equus caballus
<220> FEATURE:
<221> NAME/KEY: Peptide
<222> LOCATION: (1)..(28)
<223> OTHER INFORMATION: Amino acid sequence for equine endogenous
      peptides of growth hormone secretagogue

<400> SEQUENCE: 21

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25
```